(12) United States Patent
Monson et al.

(10) Patent No.: US 11,690,114 B2
(45) Date of Patent: Jun. 27, 2023

(54) WIRELESS LINK PAIRING AUTHENTICATION

(71) Applicant: LIKO RESEARCH & DEVELOPMENT AB, Luleå (SE)

(72) Inventors: Gavin M. Monson, Oxford, OH (US); Douglas A. Seim, Okeana, OH (US); Bryan Weidman, Columbus, IN (US); Eric Benz, Sunman, IN (US); Todd P. O'Neal, Fairfield, OH (US); Joseph T. Canter, Harrison, OH (US); Gregory J. Shannon, Indianapolis, IN (US); Jason M. Williams, Cary, NC (US); Scott M. Corbin, Sunman, IN (US)

(73) Assignee: LIKO RESEARCH & DEVELOPMENT AB, Luleå (SE)

( * ) Notice: Subject to any disclaimer, the term of this patent is extended or adjusted under 35 U.S.C. 154(b) by 0 days.

(21) Appl. No.: 17/538,337

(22) Filed: Nov. 30, 2021

(65) Prior Publication Data
US 2022/0095399 A1    Mar. 24, 2022

Related U.S. Application Data

(63) Continuation of application No. 16/889,259, filed on Jun. 1, 2020, now Pat. No. 11,240,857.
(Continued)

(51) Int. Cl.
*H04W 76/14*  (2018.01)
*H04W 76/11*  (2018.01)
(Continued)

(52) U.S. Cl.
CPC ........... *H04W 76/14* (2018.02); *H04W 12/06* (2013.01); *H04W 72/04* (2013.01); *H04W 76/11* (2018.02)

(58) Field of Classification Search
CPC ....... H04W 8/005; H04W 4/80; H04W 12/50; H04W 84/18; H04W 12/06; H04W 48/10;
(Continued)

(56) References Cited

U.S. PATENT DOCUMENTS 7,598,853 B2   10/2009  Becker et al.
7,636,549 B2   12/2009  Ma et al.
(Continued)

FOREIGN PATENT DOCUMENTS

EP    3179973 B1    5/2019
EP    2895130 B1    6/2019
EP    3582225 A1   12/2019

OTHER PUBLICATIONS

Extended European Search Report for European Application No. 20174663.3 dated Sep. 24, 2020, 7 pgs.

*Primary Examiner* — Kwasi Karikari
(74) *Attorney, Agent, or Firm* — Dinsmore & Shohl LLP

(57) ABSTRACT

Systems and methods include a medical device that matches an identifier received over its optical channel and associated with a control device within a line-of-sight of the medical device with an identifier received over its wireless channel and that automatically pairs with the control device associated with the matching identifier over its wireless channel, as well as, a control device that matches an identifier received over its optical channel and associated with a medical device within a line-of-sight of the control device with an identifier received over its wireless channel and that automatically pairs with the medical device associated with the matching identifier over its wireless channel, as well as, a first device and a second device that automatically pair over a wireless channel based on a location identifier received over an optical channel from a transmitter within a line-of-sight of the first device and the second device.

18 Claims, 9 Drawing Sheets

Related U.S. Application Data

(60) Provisional application No. 62/856,930, filed on Jun. 4, 2019.

(51) Int. Cl.
  *H04W 12/06* (2021.01)
  *H04W 72/04* (2023.01)

(58) Field of Classification Search
  CPC ..... H04W 76/10; H04W 12/08; H04W 12/63; H04W 12/068; H04W 84/20; H04W 12/03; H04W 12/55; H04W 4/14; H04W 4/38; H04W 40/246
  See application file for complete search history.

(56) References Cited

U.S. PATENT DOCUMENTS

| | | | |
|---|---|---|---|
| 8,102,254 B2 | 1/2012 | Becker et al. | |
| 8,319,633 B2 | 11/2012 | Becker et al. | |
| 8,515,070 B2 | 8/2013 | Juels et al. | |
| 8,674,826 B2 | 3/2014 | Becker et al. | |
| 9,762,558 B2 | 9/2017 | Modzelewski et al. | |
| 9,966,997 B2 | 5/2018 | Hayes et al. | |
| 10,085,905 B2 | 10/2018 | Bhimavarapu et al. | |
| 10,097,948 B2 | 10/2018 | Rajapaksa et al. | |
| 10,360,787 B2 | 7/2019 | Embree et al. | |
| 10,500,401 B2 | 12/2019 | Hayes | |
| 10,679,489 B2 | 6/2020 | Bodurka et al. | |
| 2005/0085248 A1* | 4/2005 | Ballay | H04L 12/2807 455/500 |
| 2007/0184847 A1 | 8/2007 | Hansen et al. | |
| 2013/0058658 A1* | 3/2013 | Friese | G08C 23/04 398/115 |
| 2014/0141725 A1 | 5/2014 | Jesme et al. | |
| 2015/0271432 A1* | 9/2015 | Muth | H04W 12/50 348/552 |
| 2016/0021485 A1 | 1/2016 | Sallas et al. | |
| 2017/0229009 A1 | 10/2017 | Foster et al. | |
| 2018/0015218 A1* | 1/2018 | Welsch | G16H 40/63 |
| 2018/0137932 A1 | 5/2018 | Fiedler et al. | |
| 2018/0174683 A1 | 6/2018 | Franz et al. | |
| 2019/0150737 A1 | 5/2019 | Bodurka et al. | |

\* cited by examiner

WIRELESS LINK PAIRING AUTHENTICATION

CROSS-REFERENCE TO RELATED APPLICATIONS

This application in a continuation of U.S. patent application Ser. No. 16/889,259, filed Jun. 1, 2020, which claims priority to U.S. Provisional Patent Application Ser. No. 62/856,930, filed Jun. 4, 2019, entitled, "WIRELESS LINK PAIRING AUTHENTICATION," the entirety of which is incorporated by reference herein.

BACKGROUND

Field

The present disclosure generally relates to systems and/or methods for pairing a medical device and a control device, and more specifically, to systems and/or methods for pairing a medical device and a control device using a line-of-sight optical link.

Technical Background

A medical facility may include a plurality of rooms where each room may include a plurality of medical devices. Each medical device may be permanently fixed within a room or movable between the plurality of rooms. In addition, each medical device may be wirelessly controlled by a respective control device and the control device may be movable between the plurality of rooms. Accordingly, given the portable nature of medical devices and/or control devices, systems and/or methods are desirable to ensure that a particular control device is in wireless communication with a particular medical device. More specifically, if wireless links are pairable, discoverable, and/or user-configurable, such systems and/or methods are desirable to ensure that a particular controlling device is paired to a particular medical device (e.g., directly observable by a user) to prevent the unintended activation and/or control of a similar or identical medical device (e.g., located in an adjacent room) despite that similar or identical medical device's wireless link being accessible to the particular controlling device (e.g., through the room's wall).

Existing methods require some form of user intervention to either place pairable devices in a discoverable state and/or to manually select from a list of detected, pairable devices with which to pair. In such aspects, placing a device in a discoverable state may be inconvenient to the user and/or difficult for the user to remember or perform and manual selection of a device may result in the user selecting the wrong device. Ultimately, neither method is preferred since the user's focus is taken off of a subject. Accordingly, systems and/or methods are desirable for efficiently, automatically, and correctly pairing a medical device and a control device.

SUMMARY

In one aspect, an automatically pairable medical device may include: a first communication system configured to communicate via a first communication channel, a second communication system configured to communicate via a second communication channel, a processor, and a memory storing program instructions, the program instructions, when executed by the processor, causing the processor to: receive an identifier associated with a control device within a line-of-sight of the medical device over the first communication channel, receive at least one identifier associated with at least one control device over the second communication channel, determine that the identifier received over the first communication channel matches an identifier of the at least one identifier received over the second communication channel, and automatically pair with the control device associated with the matching identifier over the second communication channel.

In such an aspect, according to some embodiments, the first communication channel may be an optical communication channel and the second communication channel may be a wireless communication channel. Further in such embodiments, the optical communication channel may be an infrared (IR) communication channel and the wireless communication channel may be a radio frequency (RF) communication channel. In other embodiments, the program instructions may further cause the processor to: receive control inputs from the control device associated with the matching identifier, the control inputs for controlling a function of the medical device. In yet other embodiments, the program instructions may further cause the processor to: determine that at least one of the first communication channel or the second communication channel is associated with a signal below a predetermined threshold strength, and disassociate from the control device associated with the matching identifier. In further embodiments, the control device associated with the matching identifier may be a first control device associated with a first identifier, and the program instructions may further cause the processor to: receive a second identifier associated with a second control device within the line-of-sight of the medical device over the first communication channel, determine whether the first identifier is detectable over the first communication channel, and remain paired with the first control device if the first identifier is detected over the first communication channel, or automatically disassociate from the first control device if the first identifier is not detected over the first communication channel. Further in such embodiments, the program instructions may further cause the processor to: determine that the second identifier received over the first communication channel matches an identifier of the at least one identifier received over the second communication channel, and automatically pair with the second control device associated with the matching second identifier over the second communication channel.

In another aspect, an automatically pairable control device may include: a first communication system configured to communicate via a first communication channel, a second communication system configured to communicate via a second communication channel, a processor, and a memory storing program instructions, the program instructions, when executed by the processor, causing the processor to: receive an identifier associated with a medical device within a line-of-sight of the control device over the first communication channel, receive at least one identifier associated with at least one medical device over the second communication channel, determine that the identifier received over the first communication channel matches an identifier of the at least one identifier received over the second communication channel, and automatically pair with the medical device associated with the matching identifier over the second communication channel.

In such another aspect, according to some embodiments, the first communication channel may be an optical communication channel and the second communication channel may be a wireless communication channel. Further in such embodiments, the optical communication channel may be an infrared (IR) communication channel and the wireless communication channel may be a radio frequency (RF) communication channel. In other embodiments, the program instructions may further cause the processor to: transmit control inputs to the medical device associated with the matching identifier, the control inputs for controlling a function of the medical device. In yet other embodiments, the program instructions may further cause the processor to: determine that at least one of the first communication channel or the second communication channel is associated with a signal below a predetermined threshold strength, and disassociate from the medical device associated with the matching identifier. In further embodiments, the medical device associated with the matching identifier may be a first medical device associated with a first identifier, and the program instructions may further cause the processor to: receive a second identifier associated with a second medical device within the line-of-sight of the control device over the first communication channel, determine whether the first identifier is detectable over the first communication channel, and remain paired with the first medical device if the first identifier is detected over the first communication channel, or automatically disassociate from the first medical device if the first identifier is not detected over the first communication channel. Further in such embodiments, the program instructions may further cause the processor to: determine that the second identifier received over the first communication channel matches an identifier of the at least one identifier received over the second communication channel, and automatically pair with the second medical device associated with the matching second identifier over the second communication channel. Yet further embodiments may include a user interface system including at least one user interface control, and the program instructions may further cause the processor to: receive a control input via the at least one user interface control, send an inquiry token to the medical device associated with the matching identifier over the first communication channel, determine whether a response token has been received from the first medical device associated with the matching identifier over the first communication channel, and transmit the control input to the medical device associated with the matching identifier if the response token has been received over the first communication channel, or abstain from transmitting the control input to the medical device associated with the matching identifier if the response token has not been received over the first communication channel. Yet another embodiment may include a visual indicator, and the program instructions may further cause the processor to: update the visual indicator to reflect that the medical device is not within a line-of-sight of the control device.

In a further aspect, a system for automatically pairing devices may include: a transmitter positioned within a location, the transmitter configured to transmit a location identifier over a first communication channel to devices with a line-of-sight of the transmitter, a first device configured to: receive the location identifier over the first communication channel, and transmit the location identifier and an identifier associated with the first device over a second communication channel, a second device configured to: receive the location identifier over the first communication channel, and transmit the location identifier and an identifier associated with the second device over the second communication channel, where the first device is further configured to: scan the second communication channel for the location identifier received over the first communication channel, determine that the location identifier received over the first communication channel matches a location identifier on the second communication channel, determine the second device identifier associated with the matching location identifier, and automatically pair with the second device associated with the second device identifier over the second communication channel, and where the second device is further configured to: scan the second communication channel for the location identifier received over the first communication channel, determine that the location identifier received over the first communication channel matches a location identifier on the second communication channel, determine the first device identifier associated with the matching location identifier, and automatically pair with the first device associated with the first device identifier over the second communication channel.

In such a further aspect, according to some embodiments, the first communication channel may be an optical communication channel and the second communication channel may be a wireless communication channel. Further in such embodiments, the optical communication channel may be an infrared (IR) communication channel and the wireless communication channel may be a radio frequency (RF) communication channel. In other embodiments, the first communication channel may be an ultra-wide band communication channel.

In yet another aspect, a method for automatically pairing a medical device with a control device may include: receiving, via a first communication channel, an identifier associated with a control device within a line-of-sight of the medical device, receiving, via a second communication channel different from the first communication channel, at least one identifier associated with at least one control device, determining that the identifier received over the first communication channel matches an identifier of the at least one identifier received over the second communication channel, and automatically pairing with the control device associated with the matching identifier over the second communication channel.

In such yet another aspect, according to some embodiments, the first communication channel may be an optical communication channel and the second communication channel may be a wireless communication channel. Further in such embodiments, the optical communication channel may be an infrared (IR) communication channel and the wireless communication channel may be a radio frequency (RF) communication channel. In other embodiments, the method may further include: receiving control inputs from the control device associated with the matching identifier, the control inputs for controlling a function of the medical device. In yet other embodiments, the method may further include: determining that at least one of the first communication channel or the second communication channel is associated with a signal below a predetermined threshold strength, and disassociating from the control device associated with the matching identifier. In further embodiments, the control device associated with the matching identifier may be a first control device associated with a first identifier, and the method may further include: receiving, via the first communication channel, a second identifier associated with a second control device within the line-of-sight of the medical device, determining whether the first identifier is detectable over the first communication channel, and remaining paired with the first control device if the first identifier is detected over the first communication channel, or automatically disassociating from the first control device if the first identifier is not detected over the first communication channel. Further in such embodiments, the method may further include: determining that the second identifier received over the first communication channel matches an identifier of the at least one identifier received over the second communication channel, and automatically pairing with the second control device associated with the matching second identifier over the second communication channel.

In yet a further aspect, a method for automatically pairing a control device with a medical device may include: receiving, via a first communication channel, an identifier associated with a medical device within a line-of-sight of the control device, receiving, via a second communication channel different from the first communication channel, at least one identifier associated with at least one medical device, determining that the identifier received over the first communication channel matches an identifier of the at least one identifier received over the second communication channel, and automatically pairing with the medical device associated with the matching identifier over the second communication channel.

In such yet a further aspect, according to some embodiments, the first communication channel may be an optical communication channel and the second communication channel may be a wireless communication channel. Further in such embodiments, the optical communication channel may be an infrared (IR) communication channel and the wireless communication channel may be a radio frequency (RF) communication channel. In other embodiments, the method may further include: transmitting control inputs to the medical device associated with the matching identifier, the control inputs for controlling a function of the medical device. In yet other embodiments, the method may further include: determining that at least one of the first communication channel or the second communication channel is associated with a signal below a predetermined threshold strength, and disassociating from the medical device associated with the matching identifier. In further embodiments, the medical device associated with the matching identifier may be a first medical device associated with a first identifier, and the method may further include: receiving, via the first communication channel, a second identifier associated with a second medical device within the line-of-sight of the control device, determining whether the first identifier is detectable over the first communication channel, and remaining paired with the first medical device if the first identifier is detected over the first communication channel, or automatically disassociating from the first medical device if the first identifier is not detected over the first communication channel. Further in such embodiments, the method may further include: determining that the second identifier received over the first communication channel matches an identifier of the at least one identifier received over the second communication channel, and automatically pairing with the second medical device associated with the matching second identifier over the second communication channel. In yet further embodiments, the method may further include: receiving, via at least one user interface control, a control input, sending, via the first communication channel, an inquiry token to the medical device associated with the matching identifier, determining, via the first communication channel, whether a response token has been received from the first medical device associated with the matching identifier, and transmitting the control input to the medical device associated with the matching identifier if the response token has been received over the first communication channel, or abstaining from transmitting the control input to the medical device associated with the matching identifier if the response token has not been received over the first communication channel. In yet another embodiment, the method may further include: updating a visual indicator to reflect that the medical device is not within a line-of-sight of the control device.

In still a further aspect, a method for automatically pairing devices may include: transmitting, via a transmitter positioned within a location, a location identifier over a first communication channel to devices with a line-of-sight of the transmitter, receiving, by a first device and a second device, the location identifier over the first communication channel, transmitting, by the first device, the location identifier and an identifier associated with the first device over a second communication channel, transmitting, by the second device, the location identifier and an identifier associated with the second device over the second communication channel, scanning, by the first device and the second device, the second communication channel for the location identifier received over the first communication channel, determining, by the first device and the second device, that the location identifier received over the first communication channel matches a location identifier on the second communication channel, determining, by the first device, the second device identifier associated with the matching location identifier and automatically pairing with the second device associated with the second device identifier over the second communication channel, and determining, by the second device, the first device identifier associated with the matching location identifier, and automatically pairing with the first device associated with the first device identifier over the second communication channel.

In such still a further aspect, according to some embodiments, the first communication channel may be an optical communication channel and the second communication channel may be a wireless communication channel. Further in such embodiments, the optical communication channel may be an infrared (IR) communication channel and the wireless communication channel may be a radio frequency (RF) communication channel. In other embodiments, the first communication channel is an ultra-wide band communication channel.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
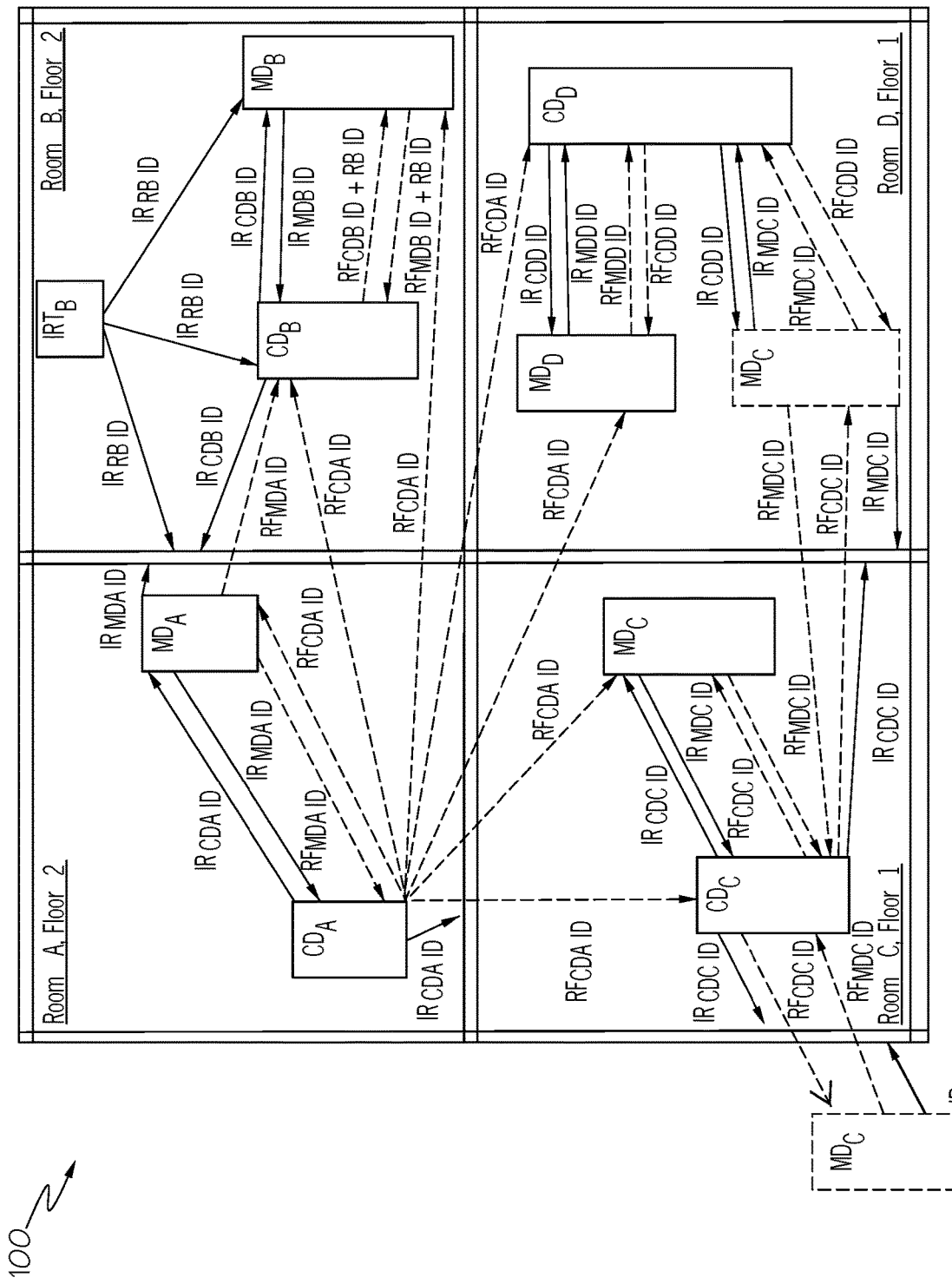
FIG. 1 depicts a block diagram illustrating a plurality of control devices and a plurality of medical devices distributed amongst a plurality of rooms and a plurality of floors of a medical facility, according to one or more embodiments shown and described herein.

Reference will now be made in detail to embodiments to pair a medical device and a control device using a line-of-sight optical link, examples of which are illustrated in the accompanying drawings. Whenever possible, the same reference numerals will be used throughout the drawings to refer to the same or like parts. Various embodiments of the present disclosure are depicted in FIG. 1. In general, a medical facility 100 may include a plurality of rooms and/or a plurality of floors (e.g., Rooms A and B on Floor 2 and Rooms C and D on Floor 1). In such aspects, a plurality of medical devices (e.g. $MD_A$, $MD_B$, $MD_C$, and/or $MD_D$) and a plurality of control devices (e.g., $CD_A$, $CD_B$, $CD_C$, and/or $CD_D$) may be distributed amongst the rooms and/or floors (see FIG. 1).

In one aspect, referring to FIG. 1, a control device (e.g., $CD_A$) and a medical device (e.g., $MD_A$) may be fixedly positioned within a room (e.g., Room A) and in line-of-sight of one another. Line-of-sight, for example, may refer to an arrangement such that an optical system (e.g., IR system) of a medical device and an optical system (e.g., IR system) of a control device have an unobstructed view of each other for emitted radiation (e.g., IR) to travel therebetween along a straight line or path. According to such an aspect, the control device (e.g., $CD_A$) may wirelessly transmit (e.g., via a Bluetooth RF signal) its identifier (e.g., $CD_A$ ID). Since a wireless signal may penetrate the walls and/or floors of the medical facility 100, a number of medical devices ($MD_A$, $MD_B$, $MD_C$, $MD_D$, and/or the like) and/or a number of control devices (e.g., $CD_B$, $CD_C$, $CD_D$, and/or the like) within range (e.g., up to 300 feet for Class 1 Bluetooth, up to 33 feet for Class 2 Bluetooth, and/or the like) may wirelessly receive the identifier (e.g., $CD_A$ ID). Further in such an aspect, the control device (e.g., $CD_A$) may optically transmit (e.g., via an IR optical signal) its identifier (e.g., $CD_A$ ID) to medical devices (e.g., $MD_A$) within its line-of-sight. Since an optical signal cannot penetrate the walls and/or the floors of the medical facility 100, the control device (e.g., $CD_A$) is only able to optically transmit its identifier (e.g., $CD_A$ ID) to medical devices within its room (e.g., $MD_A$ in Room A). Yet further in such an aspect, each medical device (e.g., $MD_A$) optically receiving a control device identifier (e.g., $CD_A$ ID) via its optical communication channel (e.g., IR channel) may be configured to scan its wireless communication channel (e.g., RF channel) to determine whether the control device identifier (e.g., $CD_A$ ID) optically received via its optical communication channel (e.g., IR channel) matches a control device identifier wirelessly received via its wireless communication channel (e.g., RF channel). If a match exists, each medical device (e.g., $MD_A$) may be configured to automatically authenticate the control device (e.g., $CD_A$) corresponding to the matching identifier (e.g., $CD_A$ ID) and to pair with the authenticated control device (e.g., $CD_A$). After such an authenticated pairing (e.g., one-way authentication), each medical device (e.g., $MD_A$) may be configured to receive control signals from the authenticated control device (e.g., $CD_A$) over its wireless communication channel (e.g., RF channel). In some aspects, after such an authenticated pairing (e.g., one-way authentication), each medical device (e.g., $MD_A$) may be configured to receive control signals from the authenticated control device (e.g., $CD_A$) over its optical communication channel (e.g., IR channel). Still referring to FIG. 1, medical devices (e.g., $MD_B$, $MD_C$, $MD_D$, and/or the like) that are not within a line-of-sight of the control device (e.g., $CD_A$) will not optically receive the optically transmitted identifier (e.g., $CD_A$ ID) and thus will not be triggered to scan their respective wireless communication channels for a matching control device identifier.

In another aspect, referring to FIG. 1, a medical device (e.g., $MD_A$) and a control device (e.g., $CD_A$) may be fixedly positioned within a room (e.g., Room A) and in line-of-sight of one another. According to such an aspect, the medical device (e.g., $MD_A$) may wirelessly transmit (e.g., via a Bluetooth RF signal) its identifier (e.g., $MD_A$ ID). Again, since a wireless signal may penetrate the walls and/or floors of the medical facility 100, a number of medical devices and/or a number of control devices (e.g., $CD_B$, and/or the like) within range may wirelessly receive the identifier (e.g., $MD_A$ ID). Further in such an aspect, the medical device (e.g., $MD_A$) may optically transmit (e.g., via an IR optical signal) its identifier (e.g., $MD_A$ ID) to control devices (e.g., $CD_A$) within its line-of-sight. Again, since an optical signal cannot penetrate the walls and/or the floors of the medical facility 100, the medical device (e.g., $MD_A$) is only able to optically transmit its identifier (e.g., $MD_A$ ID) to control devices within its room (e.g., $CD_A$ in Room A). Yet further in such an aspect, each control device (e.g., $CD_A$) optically receiving a medical device identifier (e.g., $MD_A$ ID) via its optical communication channel (e.g., IR channel) may be configured to scan its wireless communication channel (e.g., RF channel) to determine whether the medical device identifier (e.g., $MD_A$ ID) optically received via its optical communication channel (e.g., IR channel) matches a medical device identifier wirelessly received via its wireless communication channel (e.g., RF channel). If a match exists, each control device (e.g., $CD_A$) may be configured to automatically authenticate the medical device (e.g., $MD_A$) corresponding to the matching identifier (e.g., $MD_A$ ID) and to pair with the authenticated medical device (e.g., $MD_A$). After such an authenticated pairing (e.g., one-way authentication), each control device (e.g., $CD_A$) may be configured to transmit control signals to the authenticated medical device (e.g., $MD_A$) over its wireless communication channel (e.g., RF channel). In some aspects, after such an authenticated pairing (e.g., one-way authentication), each control device (e.g., $CD_A$) may be configured to transmit control signals to the authenticated medical device (e.g., $MD_A$) over its optical communication channel (e.g., IR channel).

In yet another aspect, referring to FIG. 1, the medical device (e.g., $MD_A$) may authenticate the control device (e.g., $CD_A$) and the control device (e.g., $CD_A$) may authenticate the medical device (e.g., $MD_A$) as described above. In such an aspect (e.g., two-way authentication), only after the medical device (e.g., $MD_A$) pairs to the authenticated control device (e.g., $CD_A$) and the control device (e.g., $CD_A$) pairs to the authenticated medical device (e.g., $MD_A$), may the control device (e.g., $CD_A$) transmit control signals to the medical device (e.g., $MD_A$) and the medical device (e.g., $MD_A$) receive control signals from the control device (e.g., $CD_A$). For purposes of simplification, it should be appreciated that the various embodiments described herein may employ either one-way authentication or two-way authentication without departing from the spirit and scope of the present disclosure.

In another aspect, referring to FIG. 1, a control device (e.g., $CD_C$) and a medical device (e.g., $MD_C$) may not be fixedly positioned within a room (e.g., Room C) and may not be within line-of-sight of one another. According to such an aspect, the control device (e.g., $CD_C$) may wirelessly transmit (e.g., via a Bluetooth RF signal) its identifier (e.g., $CD_C$ ID) and a medical device (e.g., $MD_C$) positioned outside of the room (e.g., Room C) and not within line-of-sight of any other control device (e.g., $CD_A$, $CD_B$, $CD_D$, and/or the like) may wirelessly receive the identifier (e.g., $CD_C$ ID). Similar to above, the control device (e.g., $CD_C$) may optically transmit (e.g., via an IR optical signal) its identifier (e.g., $CD_C$ ID). However, in view of FIG. 1, since the medical device (e.g., $MD_C$) is not yet within a line-of-sight of the control device (e.g., $CD_C$) the medical device (e.g., $MD_C$) will not optically receive the control device identifier (e.g., $CD_C$ ID) and will not be triggered to scan its wireless communication channel for a matching control device identifier. However, after repositioning the medical device (e.g., $MD_C$) within the room (e.g., Room C) and within the line-of-sight of the control device (e.g., $CD_C$), the medical device (e.g., $MD_C$) may optically receive the control device identifier (e.g., $CD_C$ ID) via its optical communication channel and may be triggered to scan its wireless communication channel for a matching control device identifier as well as automatically authenticate and pair with the control device (e.g., $CD_C$) associated with a matching control device identifier (e.g., $CD_C$ ID). The medical device (e.g., $MD_C$) may then be configured to receive control inputs from the authenticated control device (e.g. $CD_C$) over its wireless communication channel. Yet further, in view of FIG. 1, the medical device (e.g., $MD_C$), after being paired with an authenticated control device (e.g., $CD_C$) may be repositioned within another room (e.g., Room D) without a line-of-sight of the control device (e.g., $CD_C$). According to various aspects of the present disclosure, after being paired with an authenticated control device (e.g., $CD_C$), a medical device (e.g., $MD_C$) may be further configured to monitor its optical communication channel for the authenticated control device identifier (e.g., $CD_C$ ID). In such an aspect, if the control device identifier (e.g., $CD_C$ ID) is no longer being received over its optical communication channel, the medical device (e.g., $MD_C$) may be configured to automatically disassociate from the control device (e.g., $CD_C$) over its wireless communication channel. However, after repositioning the medical device (e.g., $MD_C$) within another room (e.g., Room D) and within the line-of-sight of another control device (e.g., $CD_D$), the medical device (e.g., $MD_C$) may optically receive the control device identifier (e.g., $CD_D$ ID) via its optical communication channel and may be triggered to scan its wireless communication channel for a matching control device identifier as well as automatically authenticate and pair with the control device (e.g., $CD_D$) associated with a matching control device identifier (e.g., $CD_D$ ID). The medical device (e.g., $MD_C$) may then be configured to receive control inputs from the newly authenticated control device (e.g. $CD_D$) over its wireless communication channel. In such various aspects, although not specifically described, it should be appreciated that the control devices (e.g., $CD_C$, $CD_D$) may alternatively authenticate and pair with the medical device (e.g., $MD_C$) via one-way authentication or the medical device (e.g., $MD_C$) may authenticate and pair with the control devices (e.g., $CD_C$, $CD_D$) and the control devices (e.g., $CD_C$, $CD_D$) may authenticate and pair with the medical device (e.g., $MD_C$) via two-way authentication. Furthermore, similar to as described above, after being paired with an authenticated medical device (e.g., $MD_C$), the control devices (e.g., $CD_C$, $CD_D$) may be further configured to monitor their respective optical communication channels for the authenticated medical device identifier (e.g., $MD_C$ ID). In such an aspect, if the medical device identifier (e.g., $MD_C$ ID) is no longer being received over their respective optical communication channels, the control devices (e.g., $CD_C$, $CD_D$) may be configured to automatically disassociate from the medical device (e.g., $MD_C$) over their respective wireless communication channels.

In a further aspect, a control device (e.g., $CD_D$) and a medical device (e.g., $MD_D$) may not be fixedly positioned within a room (e.g., Room D). For example, referring to FIG. 1, although the medical device (e.g., $MD_D$) may be repositioned, it may remain positioned within the line-of-sight of the control device (e.g., $CD_D$). Accordingly, the control device (e.g., $CD_D$) and the ($MD_D$) may be authentically paired with one another as described herein (e.g., one-way authentication, two-way authentication). In this vein, as described herein, another medical device (e.g., $MD_C$) may be positioned within the line-of-sight of the control device (e.g., $CD_D$) in the room (e.g., Room D). Accordingly, the control device (e.g., $CD_D$) may optically receive another medical device identifier (e.g., $MD_C$ ID) via its optical communication channel (e.g., IR channel). In such an aspect, the control device (e.g., $CD_D$) may be configured to monitor its optical communication channel for the authenticated medical device identifier (e.g., $MD_D$ ID). In one example, if the authenticated medical device identifier (e.g., $MD_D$ ID) is still being received over its optical communication channel, the control device (e.g., $CD_D$) may be configured to remain authentically paired to the medical device (e.g., $MD_D$) and ignore the presence of the other medical device (e.g., $MD_C$). In an alternative example, if the authenticated medical device identifier (e.g., $MD_D$ ID) is still being received over its optical communication channel, the control device (e.g., $CD_D$) may be configured to further authenticate and pair with the other medical device (e.g., $MD_C$).

In yet another aspect, referring to FIG. 1, a control device (e.g., $CD_B$) and a medical device (e.g., $MD_B$) may or may not be fixedly positioned within a room (e.g., Room B) in line-of-sight of one another. According to such an aspect, an IR transmitter (e.g., $IRT_B$) fixed within the room (e.g., Room B) may optically transmit a room identifier (e.g., RB ID) to control devices (e.g., $CD_B$) and medical devices (e.g., $MD_B$) within its line-of-sight. Again, since an optical signal cannot penetrate the walls and/or the floors of the medical facility 100, the IR transmitter (e.g., $IRT_B$) is only able to optically transmit the room identifier (e.g., RB ID) to control devices and medical devices within its room (e.g., Room B). In such an aspect, each control device (e.g., $CD_B$) that optically receives a room identifier (e.g., RB ID) via its optical communication channel (e.g., IR channel) may be configured to wirelessly transmit the received room identifier (e.g., RB ID) with its identifier (e.g., $CD_B$ ID) over its wireless communication channel (e.g., RF channel). Similarly, in such an aspect, each medical device (e.g., $MD_B$) that optically receives a room identifier (e.g., RB ID) via its optical communication channel (e.g., IR channel) may be configured to wirelessly transmit the received room identifier (e.g., RB ID) with its identifier (e.g., $MD_B$ ID) over its wireless communication channel (e.g., RF channel). In this vein, in one example, each control device (e.g., $CD_B$) that optically receives a room identifier (e.g., RB ID) via its optical communication channel may be further configured to scan its wireless communication channel to determine whether the room identifier (e.g., RB ID) optically received via its optical communication channel matches a room identifier wirelessly received via its wireless communication channel. If a match exists, each control device (e.g., $CD_B$) may be configured to automatically authenticate a medical device (e.g., $MD_B$) corresponding to the identifier (e.g., $MD_B$ ID) wirelessly received with the room identifier (e.g., RB ID) over its wireless communication channel and to pair with the authenticated medical device. After such an authenticated pairing (e.g., one-way authentication), each control device (e.g., $CD_B$) may be configured to transmit control signals to the authenticated medical device (e.g., $MD_B$) over its wireless communication channel. Similarly, in another example, each medical device (e.g., $MD_B$) that optically receives a room identifier (e.g., RB ID) via its optical communication channel may be further configured to scan its wireless communication channel to determine whether the room identifier (e.g., RB ID) optically received via its optical communication channel matches a room identifier wirelessly received via its wireless communication channel. If a match exists, each medical device (e.g., $MD_B$) may be configured to automatically authenticate a control device (e.g., $CD_B$) corresponding to the identifier (e.g., $CD_B$ ID) wirelessly received with the room identifier (e.g., RB ID) over its wireless communication channel and to pair with the authenticated control device. After such an authenticated pairing (e.g., one-way authentication), each medical device (e.g., $MD_B$) may be configured to receive control signals from the authenticated control device (e.g., $CD_B$) over its wireless communication channel. Yet further, in another example, the control device (e.g., $CD_B$) may authenticate the medical device (e.g., $MD_B$) and the medical device (e.g., $MD_B$) may authenticate the control device (e.g., $CD_B$) as described. In such an aspect (e.g., two-way authentication), only after the control device (e.g., $CD_B$) pairs to the authenticated medical device (e.g., $MD_B$) and the medical device (e.g., $MD_B$) pairs to the authenticated control device (e.g., $CD_B$), may the control device (e.g., $CD_B$) transmit control signals to the medical device (e.g., $MD_B$) and the medical device (e.g., $MD_B$) receive control signals from the control device (e.g., $CD_B$). Still referring to FIG. 1, medical devices (e.g., $MD_A$, $MD_C$, $MD_D$, and/or the like) and control devices (e.g., $CD_A$, $CD_C$, $CD_D$, and/or the like) that are not within a line-of-sight of the IR transmitter (e.g., $IRT_B$) will not optically receive the optically transmitted room identifier (e.g., RB ID) and thus will not be triggered to scan their respective wireless communication channels for a matching room identifier.

According to alternative aspects of the present disclosure, the optical communication channel as described herein may be supplanted by or used in combination with another communication channel (e.g., a different non-RF communication channel, a non-audible (e.g., ultrasonic) communication channel, and/or the like) without departing from the spirit and scope of the present disclosure.

Figure 2A:
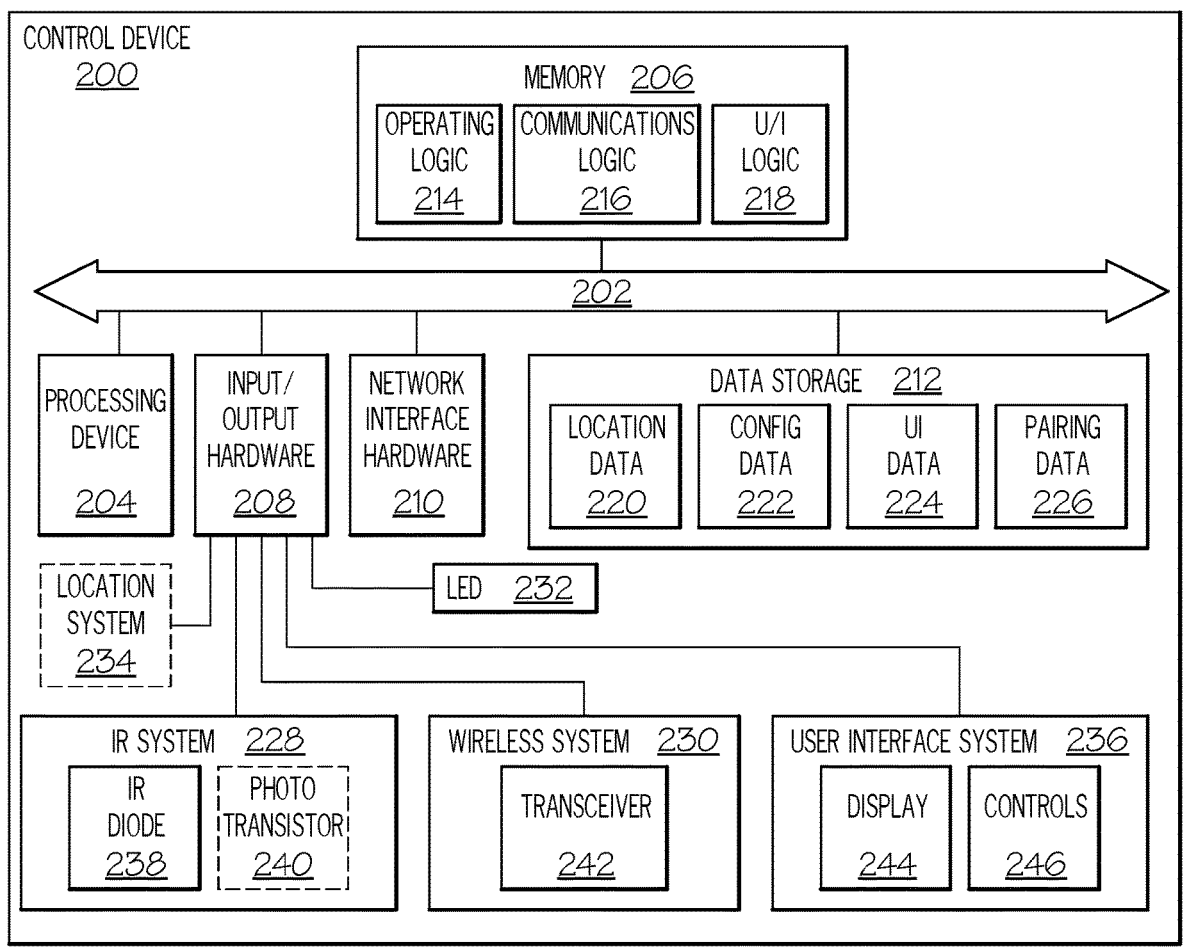
FIG. 2A depicts illustrative internal components of a control device that are communicatively coupled to one another to provide wireless link pairing authentication with a medical device, according to one or more embodiments shown and described herein.

FIG. 2A depicts illustrative internal components of a control device 200 that are communicatively coupled to one another to provide wireless link pairing authentication with a medical device, according to one or more embodiments of the present disclosure. As shown in FIG. 2A, the control device 200 may include a local interface 202 (e.g., a bus) that communicatively interconnects the various components, including, but not limited to, a processing device 204, memory 206, input/output hardware 208, network interface hardware 210, and/or a data storage device 212.

The processing device 204, such as a computer processing unit (CPU), may be the central processing unit of the control device 200, performing calculations and logic operations required to execute a program. The processing device 204, alone or in conjunction with one or more of the other elements disclosed in FIG. 2A, is an illustrative processing device, computing device, processor, or combination thereof, as such terms are used in this disclosure.

The memory 206, such as read only memory (ROM) and random access memory (RAM), may constitute illustrative memory devices (i.e., non-transitory, processor-readable storage media). Such memory 206 may include one or more programming instructions thereon that, when executed by the processing device 204, cause the processing device 204 to complete various processes, such as the processes described herein. Optionally, the program instructions may be stored on a tangible computer-readable medium such as a digital disk, flash memory, a memory card, a USB drive, an optical disc storage medium (e.g., Blu-Ray™, CD, DVD), and/or other non-transitory processor-readable storage media.

In some embodiments, the program instructions contained on the memory 206 may be embodied as a plurality of software modules, where each module provides programming instructions for completing one or more tasks. For example, as shown in FIG. 2A, the memory 206 may contain one or more of operating logic 214, communications logic 216, and UI logic 218. It should be understood that the various logic modules described herein with respect to FIG. 2A are merely illustrative, and that other logic modules, including logic modules that combine the functionality of two or more of the modules described hereinabove, may be used without departing from the scope of the present disclosure.

Still referring to FIG. 2A, the data storage device 212, which may generally be a storage medium that is separate from the memory 206, may contain a data repository for storing electronic data and/or the like relating to the location of the control device 200, an identification of the control device 200, configuration settings, UI data, and/or the like. The data storage device 212 may be any physical storage medium, including, but not limited to, a hard disk drive (HDD), memory, removable storage, and/or the like. While the data storage device 212 is depicted as a local device, it should be understood that the data storage device 212 may be a remote storage device that is remotely located from the control device 200, such as, for example, a server computing device or the like.

Illustrative data that may be contained within the data storage device 212 may include, for example, location data 220, configuration data 222, UI data 224, pairing data 226, and/or the like. Pairing data 226 may include one or more medical device identifiers to which the control device 200 is or has been authentically paired via the methods as described herein.

The input/output hardware 208 may generally include an IR system 228, a wireless system 230, an indicator 232, a location system 234, and a user interface system 236. The IR system 228 may include an IR diode 238 (e.g., infrared LED) configured to emit/transmit infrared light and a photo transistor 240 configured to receive infrared light and to convert the infrared light into an electric current (e.g., according to IR protocols). The IR system 228 may be unidirectional (e.g., photo transistor 240 shown in phantom as optional) or bidirectional (e.g., including the photo transistor 240). Furthermore, the photo transistor 240 may be omni-directional to receive misaligned (e.g., within a defined tolerance) and/or reflected (e.g., off a wall, an object within the room, and/or the like) optical signals. According to various aspects the IR system 278 may include a transceiver module. The wireless system 230 may include a transceiver 242 configured to transmit and to receive wireless signals (e.g., RF, Bluetooth, UWB, and/or the like) according to the respective wireless protocols. According to various aspects, RF may be utilized to efficiently transfer data with fewer errors. In some aspects, data transmission techniques including encryption/decryption, forward error correction, and/or the like may be instituted. According to an alternative aspect, the wireless system 230 may be substituted with a second IR system and a multiplexer (not shown). The indicator 232 may include a light emitting diode, indicator light, and/or the like. The location system 234 may include a Global Positioning System (GPS), a Global Navigation Satellite System (GLONASS), a Wi-Fi locating system, and/or the like. The user interface system may include a display 244 and/or user interface controls 246 configured to receive control inputs for transmission via the input/output hardware 208 and to display outputs received from the input/output hardware 208.

The network interface hardware 210 may generally provide the control device 200 with an ability to interface with one or more external devices, such as, for example, a medical facility server, a nurse station, and/or the like. Communication with external devices may occur using various communication ports (not shown). An illustrative communication port may be attached to a communications network, such as the Internet, an intranet, a local network, a direct connection, and/or the like.

It should be understood that in some embodiments, the input/output hardware 208 and the network interface hardware 210 may be combined into a single device that allows for communications with other devices, regardless of whether such other devices are located within the control device 200.

It should be understood that the components illustrated in FIG. 2A are merely illustrative and are not intended to limit the scope of the present disclosure. More specifically, while the components in FIG. 2A are illustrated as residing within the control device, this is a non-limiting example. In some embodiments, one or more of the components may reside external to the control device. Similarly, one or more of the components may be embodied in other devices not specifically described herein. Furthermore, various control devices are described herein (e.g., FIG. 3) and are non-limiting examples. Other control devices may include a user's personal cell-phone, a nurse's call system device, and/or the like with auxiliary line-of-sight communication channel capabilities (e.g., adapter).

Figure 2B:
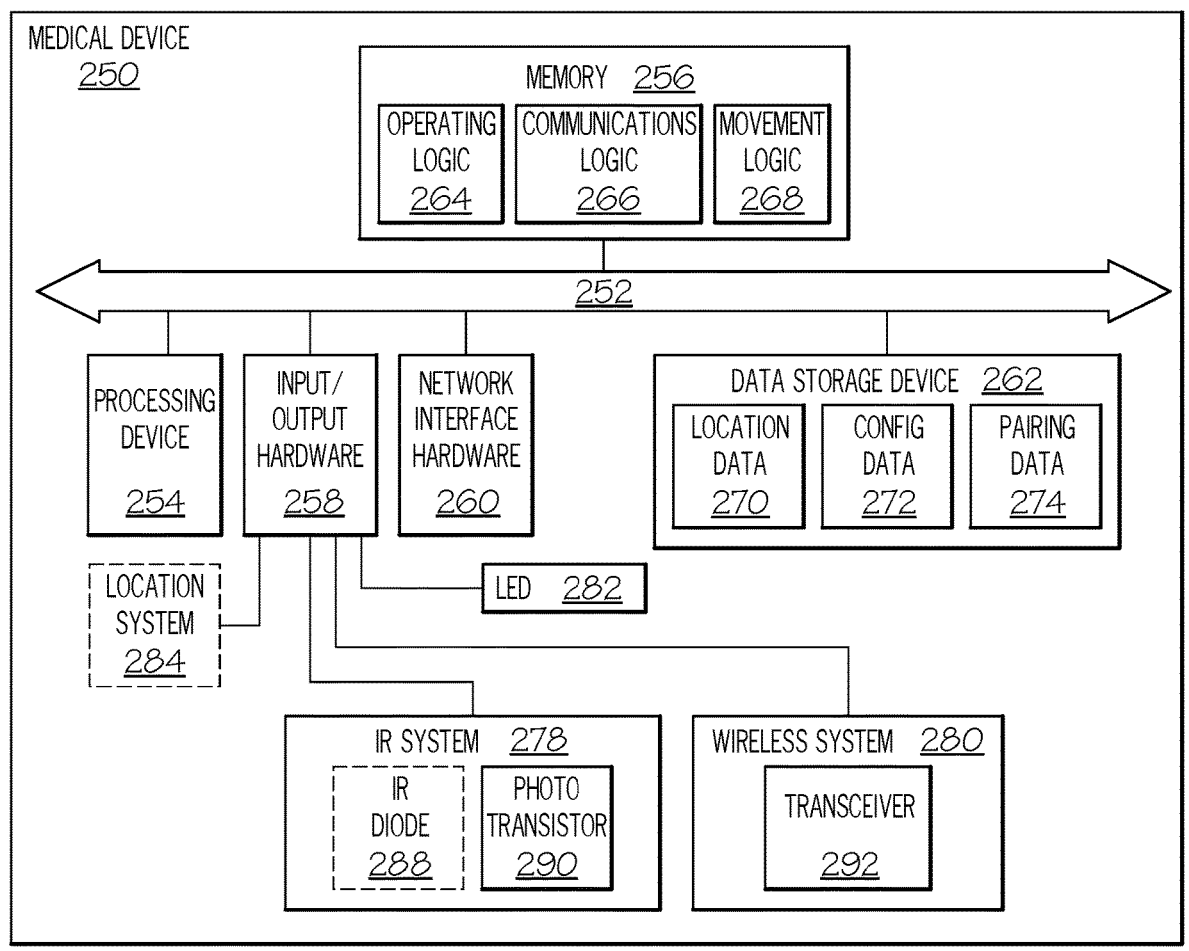
FIG. 2B depicts illustrative internal components of a medical device that are communicatively coupled to one another to provide wireless link pairing authentication with a control device, according to one or more embodiments shown and described herein.

FIG. 2B depicts illustrative internal components of a medical device 250 that are communicatively coupled to one another to provide wireless link pairing authentication with a control device, according to one or more embodiments of the present disclosure. As shown in FIG. 2B, the medical device 250 may include a local interface 252 (e.g., a bus) that communicatively interconnects the various components, including, but not limited to, a processing device 254, memory 256, input/output hardware 258, network interface hardware 260, and/or a data storage device 262.

The processing device 254, such as a computer processing unit (CPU), may be the central processing unit of the medical device 250, performing calculations and logic operations required to execute a program. The processing device 254, alone or in conjunction with one or more of the other elements disclosed in FIG. 2B, is an illustrative processing device, computing device, processor, or combination thereof, as such terms are used in this disclosure.

The memory 256, such as read only memory (ROM) and random access memory (RAM), may constitute illustrative memory devices (i.e., non-transitory, processor-readable storage media). Such memory 256 may include one or more programming instructions thereon that, when executed by the processing device 254, cause the processing device 254 to complete various processes, such as the processes described herein. Optionally, the program instructions may be stored on a tangible computer-readable medium such as a digital disk, flash memory, a memory card, a USB drive, an optical disc storage medium (e.g., Blu-Ray™, CD, DVD), and/or other non-transitory processor-readable storage media.

In some embodiments, the program instructions contained on the memory 256 may be embodied as a plurality of software modules, where each module provides programming instructions for completing one or more tasks. For example, as shown in FIG. 2B, the memory 256 may contain one or more of operating logic 264, communications logic 266, and movement logic 268. It should be understood that the various logic modules described herein with respect to FIG. 2B are merely illustrative, and that other logic modules, including logic modules that combine the functionality of two or more of the modules described hereinabove, may be used without departing from the scope of the present disclosure.

Still referring to FIG. 2B, the data storage device 262, which may generally be a storage medium that is separate from the memory 256, may contain a data repository for storing electronic data and/or the like relating to the location of the medical device 250, an identification of the medical device 250, configuration settings, and/or the like. The data storage device 262 may be any physical storage medium, including, but not limited to, a hard disk drive (HDD), memory, removable storage, and/or the like. While the data storage device 262 is depicted as a local device, it should be understood that the data storage device 262 may be a remote storage device that is remotely located from the medical device 250, such as, for example, a server computing device or the like.

Illustrative data that may be contained within the data storage device 262 may include, for example, location data 270, configuration data 272, pairing data 274, and/or the like. Pairing data 226 may include one or more control device identifiers to which the medical device 250 is or has been authentically paired via the methods as described herein.

The input/output hardware 258 may generally include an IR system 278, a wireless system 280, an indicator 282, and a location system 284. The IR system 278 may include an IR diode 288 (e.g., infrared LED) configured to emit/transmit infrared light and a photo transistor 290 configured to receive infrared light and to convert the infrared light into an electric current (e.g., according to IR protocols). The IR system 278 may be unidirectional (e.g., IR diode 288 shown in phantom as optional) or bidirectional (e.g., including the IR diode 288). Furthermore, the photo transistor 290 may be omni-directional to receive misaligned (e.g., within a defined tolerance) and/or reflected (e.g., off a wall, an object within the room, and/or the like) optical signals. According to various aspects the IR system 278 may include a transceiver module. The wireless system 280 may include a transceiver 292 configured to transmit and to receive wireless signals (e.g., RF, Bluetooth, UWB, and/or the like) according to the respective wireless protocols. According to various aspects, RF may be utilized to efficiently transfer data with fewer errors. In some aspects, data transmission techniques including encryption/decryption, forward error correction, and/or the like may be instituted. According to an alternative aspect, the wireless system 280 may be substituted with a second IR system and a multiplexer (not shown). The indicator 282 may include a light emitting diode, indicator light, and/or the like. The location system 284 may include a Global Positioning System (GPS), a Global Navigation Satellite System (GLONASS), a Wi-Fi locating system, and/or the like.

The network interface hardware 260 may generally provide the medical device 250 with an ability to interface with one or more external components, such as, for example, a medical facility server, a nurse station, and/or the like. Communication with external devices may occur using various communication ports (not shown). An illustrative communication port may be attached to a communications network, such as the Internet, an intranet, a local network, a direct connection, and/or the like.

It should be understood that in some embodiments, the input/output hardware 258 and the network interface hardware 260 may be combined into a single device that allows for communications with other devices, regardless of whether such other devices are located within the medical device 250.

It should be understood that the components illustrated in FIG. 2B are merely illustrative and are not intended to limit the scope of this disclosure. More specifically, while the components in FIG. 2B are illustrated as residing within the medical device 250, this is a non-limiting example. In some embodiments, one or more of the components may reside external to the medical device 250. Similarly, one or more of the components may be embodied in other devices not specifically described herein.

Figure 3:
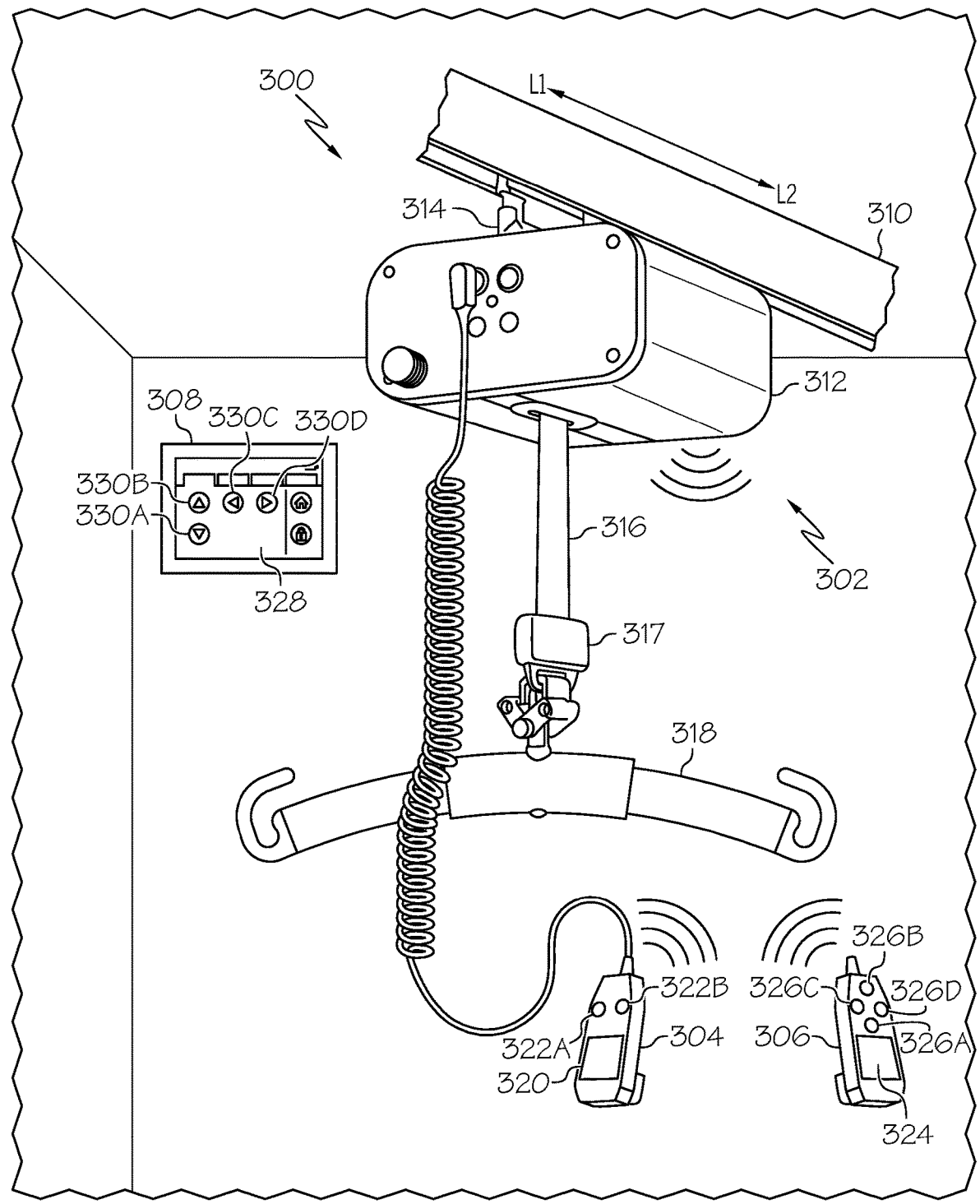
FIG. 3 depicts an illustrative wireless link pairing authentication system including a rail-mounted lift as a medical device and a tethered hand control unit, a wireless hand control unit, and/or a wall-mounted control unit as control devices, according to one or more embodiments shown and described herein.

FIG. 3 depicts an illustrative wireless link pairing authentication system 300 including a rail-mounted lift 302 as a medical device and a plurality of remote devices 304, 306, 308, as control devices, according to one or more embodiments of the present disclosure. Referring to FIG. 3, the rail-mounted lift 302 is coupled to a rail 310. According to various aspects, the rail 310 may extend along a ceiling of a room (e.g., Room A of FIG. 1), along a ceiling of more than one room (e.g., Room A and Room B of FIG. 1), and/or the like. More specifically, the rail-mounted lift 302 includes a lift unit 312 that is slidably coupled to the rail 310 via a carriage 314. The lift unit 312 may be used to support and/or lift a subject with a lifting strap 316 which is coupled to a motor (not shown) contained within the lift unit 312. The motor facilitates extending or retracting the lifting strap 316 from the lift unit 312, thereby raising and lowering a subject attached to the lifting strap 316. According to various embodiments, a subject may be attached to the lifting strap 316 with a sling bar 318 or a similar accessory attached to the lifting strap 316 via a coupling 317. The sling bar 318 or a similar accessory may be attached to a harness or a sling in which the subject is positioned, thereby facilitating the lifting operation.

Various components of the rail-mounted lift 302, such as the lift unit 312 and/or components thereof, may be operated with a tethered hand control unit 304, a wireless hand control unit 306 and/or a wall-mounted control unit 308 communicatively coupleable to the lift unit 312. In view of FIG. 3, the tethered hand control unit 304 may be directly wired to the lift unit 312 and/or wirelessly coupled or paired to the lift unit 312 (e.g., according to the methods described herein) to facilitate remote operation of the rail-mounted lift 302. According to various aspects, the tethered hand control unit 304 may include a display 320 and one or more user interface controls 322A (e.g., to extend lifting strap 316), 322B (e.g., to retract lifting strap 316). Similarly, the wireless hand control unit 306 may be wirelessly coupled or paired to the lift unit 312 (e.g., according to the methods described herein) and may include a display 324 and one or more user interface controls 326A (e.g., to extend lifting strap 316), 326B (e.g., to retract lifting strap), 326C (e.g., to translate lift unit 312 in a first lateral direction L1 along rail 310), 326D (e.g., to translate lift unit 312 in a second lateral direction L2 along rail 310), and the wall-mounted control unit 308 may be wirelessly coupled or paired to the lift unit 312 (e.g., according to the methods described herein) and may include a display 328 and one or more user interface controls 330A (e.g., to extend lifting strap 316), 330B (e.g., to retract lifting strap 316), 330C (e.g., to translate lift unit 312 in a first lateral direction L1 along rail 310), 330D (e.g., to translate lift unit 312 in a second lateral direction L2 along rail 310). Further user interface controls of the wall-mounted control unit 308 may activate the lift unit 312, pair a subject with the lift unit 312, return the lift unit 312 to a "home" position/location, receive information from the lift unit 312 (e.g., battery status, magnitude of load supported by the lift unit, and/or the like), actuate an emergency stop of the lift unit 312, reset the lift unit 312, and/or the like.

Figure 4A:
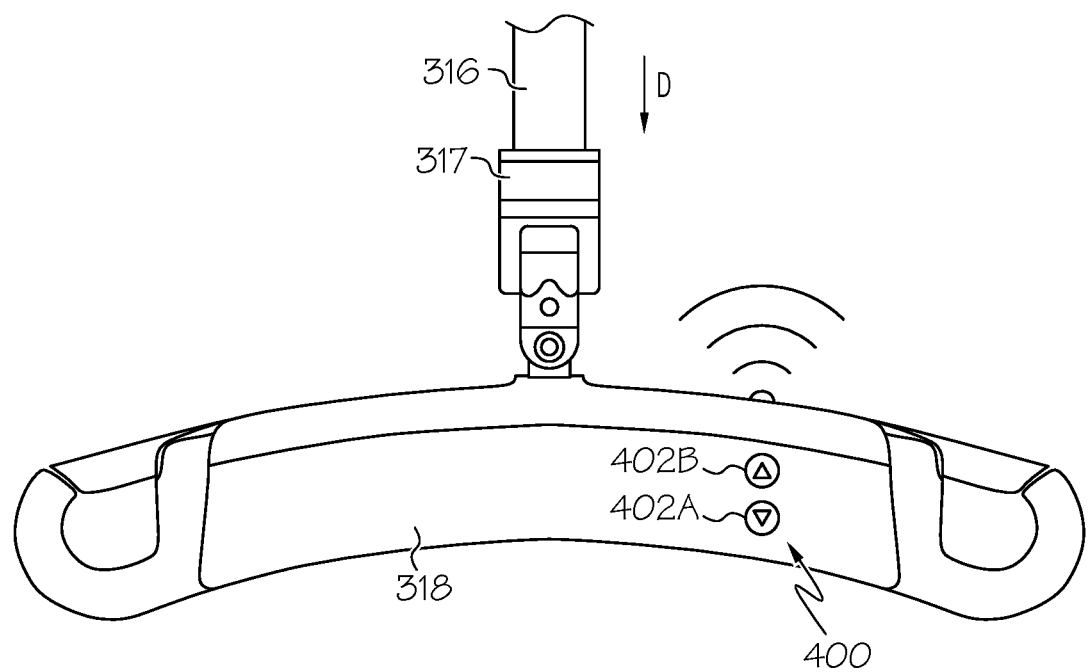
FIG. 4A depicts an illustrative sling bar control unit as a control device, according to one or more embodiments shown and described herein.
Figure 4B:
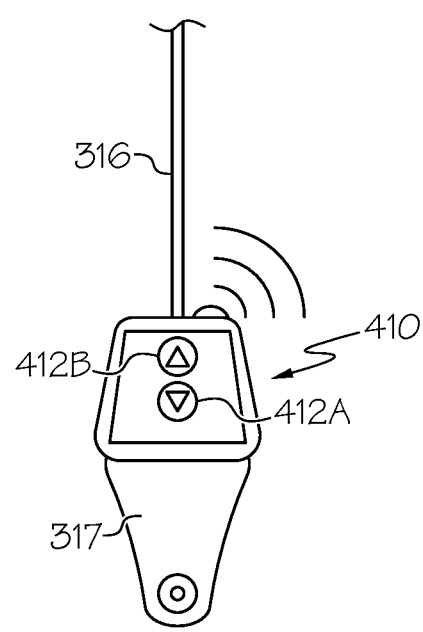
FIG. 4B depicts an illustrative coupling control unit as a control device, according to one or more embodiments shown and described herein.

Referring to FIGS. 4A and 4B, according to further aspects of the present disclosure, the rail-mounted lift 302 (e.g., FIG. 3) may be operated with a sling bar control unit 400 positioned on the sling bar 318 and/or a coupling control unit 410 positioned on the coupling 317 attached to a distal "D" end of the lifting strap 316. The sling bar control unit 400 may be wirelessly coupled or paired to the lift unit 312 (e.g., according to the methods described herein) and may include one or more user interface controls 402A (e.g., to extend lifting strap 316), 402B (e.g., to retract lifting strap 316). Similarly, the coupling control unit 410 may be wirelessly coupled or paired to the lift unit 312 (e.g., according to the methods described herein) and may include one or more user interface controls 412A (e.g., to extend lifting strap 316), 412B (e.g., to retract lifting strap 316).

In light of FIGS. 3, 4A and 4B, a plurality of control devices (e.g., a tethered hand control unit 304, a wireless hand control unit 306, a wall-mounted control unit 308, a sling bar control unit 400, a coupling control unit 410, and/or the like) may be either already physically present in a room, physically brought into the room, and/or physically taken out of the room.

According to some aspects of the present disclosure, a medical device (e.g., the rail-mounted lift 302) may be fixedly positioned within a room. In such aspects, referring to FIGS. 3 and 4B, control devices that physically remain in that room (e.g., wall-mounted control unit 308) and physically remain coupled to the medical device itself in that room (e.g., tethered hand control unit 304, coupling control unit 410), remain in the line-of-sight of the medical device and the medical device may be configured to authenticate and remain paired with all such control devices. For example, the rail-mounted lift 302 may store pairing data (FIG. 2B, reference 274, e.g., associated CD IDs in a fixed pairings file), in its data storage device (FIG. 2B, reference 262) for each control devices that physically remains in its room and/or physically remains coupled to the rail-mounted lift 302. Further in such aspects, referring to FIGS. 3 and 4A, one or more control devices may not physically remain in that room (e.g., wireless hand control unit 306, sling bar control unit 400). In such aspects, the medical device may be configured to not only authenticate and pair with such control devices as they are brought into a room but also periodically or continually monitor authenticated pairings with such control devices. Periodically, as described herein, may refer to a regularly occurring interval or time period (e.g., every "X" seconds, every "Y" minutes, and/or the like). Continuing the example, the rail-mounted lift 302 may store pairing data (e.g., FIG. 2B, reference 274, e.g., associated CD IDs in a transient pairings file), in its data storage device (e.g., FIG. 2B, reference 262) for each control device that may not physically remain in its room and the rail-mounted lift 302 may periodically determine whether each authenticated control device identifier (e.g., CD ID) is still being received over its optical communication channel. According to various aspects, if an authenticated control device identifier (e.g., stored in the transient pairings file) is still being optically received, the medical device (e.g., rail-mounted lift) may remain authentically paired with that control device and if the authenticated control device identifier is not still being optically received, the medical device may automatically disassociate from that control device (e.g., control device considered as physically taken out of the room).

Further in light of FIGS. 3, 4A, and 4B, a medical device fixedly positioned within a room may be configured to establish a hierarchy for accepting control inputs (e.g., received at or near the same time) from a plurality of authentically paired control devices. For example, the medical device may be configured to give priority to a control input received from a first grouping including control devices physically remaining in a room (e.g., a tethered hand control unit 304, a wall-mounted control unit 308, and/or a coupling control unit 410) over a control input received from a second grouping including control devices that may not physically remain in the room (e.g., a wireless hand control unit 306 and/or a sling bar control unit 400). Further in such an example, the medical device may be configured to give priority to a control input received from control devices within the first grouping (e.g., tethered hand control unit 304 over coupling control unit 410 over wall-mounted control unit 308, and/or the like) and/or control devices within the second grouping (e.g., sling bar control unit 400 over wireless hand control unit 306, and/or the like). Here, it should be appreciated that such described hierarchies are non-limiting examples and that other hierarchies may be established.

According to other aspects of the present disclosure, a medical device (e.g., a rail-mounted lift 302) may not be fixedly positioned within a room. For example, a lift unit may be moved along a rail 310 (FIG. 3) from one room (e.g., FIG. 1, Room A) to another room (e.g., FIG. 1, Room B). In such aspects, referring to FIGS. 3 and 4B, control devices that physically remain coupled to the medical device itself (e.g., tethered hand control unit 304, coupling control unit 410), remain in the line-of-sight of the medical device and the medical device may be configured to authenticate and remain paired with all such control devices. For example, the rail-mounted lift 302 may store pairing data (FIG. 2B, reference 274, e.g., associated CD IDs in a fixed pairings file), in its data storage device (FIG. 2B, reference 262) for each control devices that physically remains coupled to the rail-mounted lift 302. Further in such aspects, referring to FIGS. 3 and 4A, one or more control devices may not be physically coupled to the medical device itself. This may include control devices that physically remain in a given room (e.g., wall-mounted control units 308) and/or control devices that may not physically remain in any given room (e.g., wireless hand control unit 306, sling bar control unit 400). In such aspects, the medical device may be configured to not only authenticate and pair with such control devices but also periodically or continually monitor authenticated pairings with such control devices. Continuing the example, the rail-mounted lift 302 may store pairing data (e.g., FIG. 2B, reference 274, e.g., associated CD IDs in a transient pairings file), in its data storage device (e.g., FIG. 2B, reference 262) for each control device that physically remains in a given room and that may not physically remain in any given room and the rail-mounted lift 302 may periodically determine whether each authenticated control device identifier (e.g., CD ID) is still being received over its optical communication channel. According to various aspects, upon detecting movement (e.g., translation along rail 310) the medical device may be configured to continually monitor authenticated pairings with such control devices. Accordingly, if an authenticated control device identifier (e.g., CD ID of a wireless hand control unit 306 being used to translate or move the rail-mounted lift 302 between rooms, CD ID of a sling bar control unit 400 being moved with the rail-mounted lift 302 between rooms) is still being optically received, the medical device (e.g., rail-mounted lift) may remain authentically paired with the control device(s) and if the authenticated control device identifier (e.g., CD ID of a wall-mounted control unit 308 in a former room, CD ID of a sling bar control unit 400 not moved to a new room) is not still being optically received, the medical device may automatically disassociate from that control device(s). Further in such an aspect, the medical device may be configured to authenticate and pair with new control devices (e.g., wall-mounted control unit 308 in new room) as the medical device transitions between rooms.

Further in light of FIGS. 3, 4A, and 4B, a medical device not fixedly positioned within a room may be configured to establish a hierarchy for accepting control inputs (e.g., received at or near the same time) from a plurality of authentically paired control devices. For example, the medical device may be configured to give priority to a control input received from a first grouping including control devices that physically remain coupled to the medical device itself (e.g., a tethered hand control unit 304, a coupling control unit 410) over a control input received from a second grouping including control devices that physically remain in a given room (e.g., wall-mounted control units 308) and/or control devices that may not physically remain in any given room (e.g., wireless hand control unit 306, sling bar control unit 400). In another example, the first grouping may include a control device being used to move the medical device between rooms (e.g., wireless hand control unit 306). Here, with respect to a rail-mounted lift 302, it may be desired to use a wireless hand control unit 306 over a tethered hand control unit 304 and/or a coupling control unit 410 to move the rail-mounted lift 302 between rooms. Further in such an example, the medical device may be configured to give priority to a control input received from control devices within the first grouping (e.g., tethered hand control unit 304 or wireless hand control unit 306 over coupling control unit 410, and/or the like) and/or control devices within the second grouping (e.g., wireless hand control unit 306 over sling bar control unit 400 over wall-mounted control unit 308, and/or the like). Here, it should be appreciated that such described hierarchies are non-limiting examples and that other hierarchies may be established.

Figure 5:
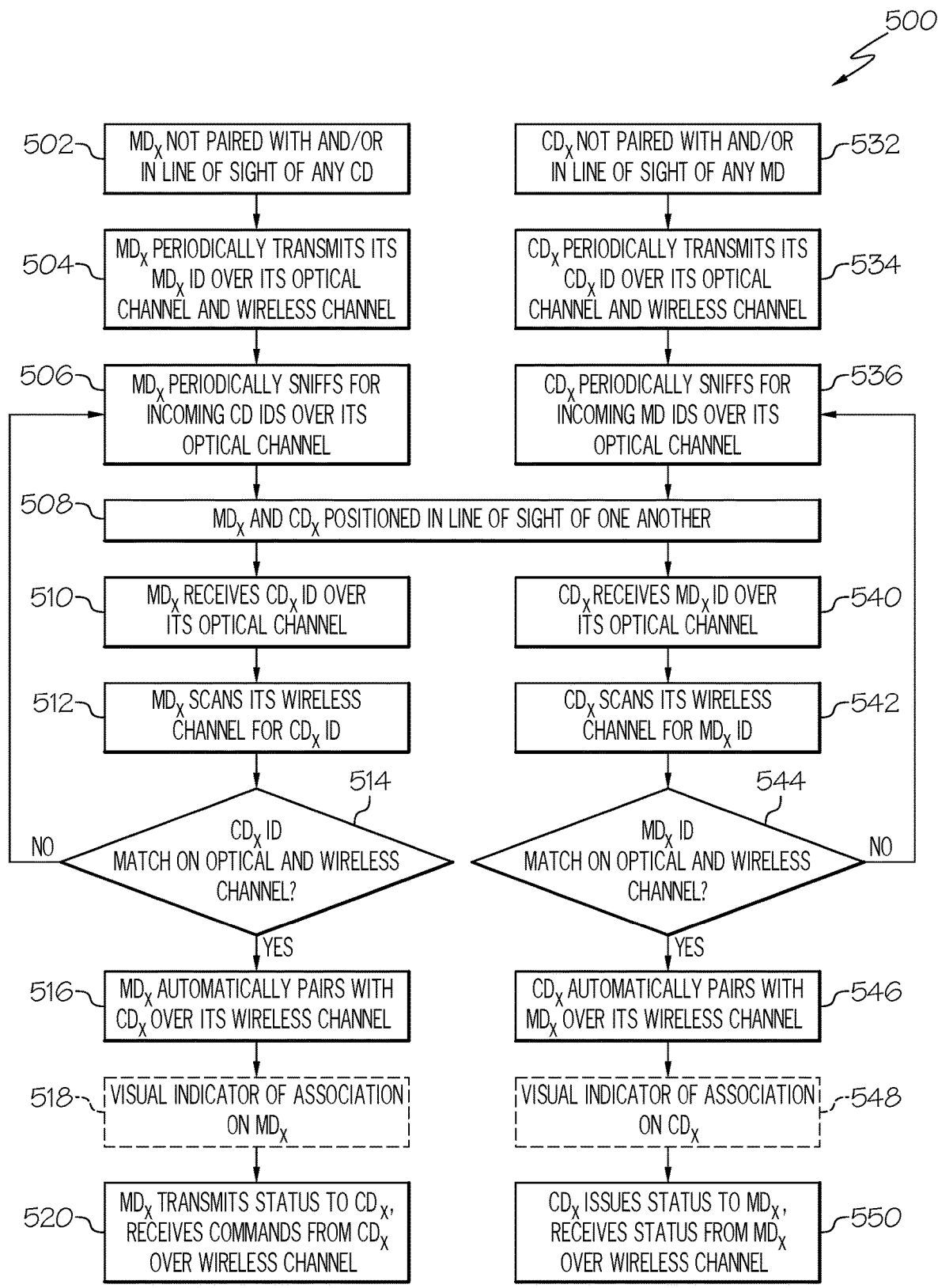
FIG. 5 depicts a flow diagram of an illustrative method for pairing a medical device and a control device using an optical communication channel, according to one or more embodiments shown and described herein.

FIG. 5 depicts a flow diagram of an illustrative method 500 for pairing a medical device and a control device using an optical communication channel, according to one or more embodiments of the present disclosure. The pairing may include a one-way authentication of the medical device with a control device (e.g., left side of FIG. 5), a one-way authentication of the control device with a medical device (e.g., right side of FIG. 5), or a two-way authentication of the medical device and the control device (e.g., both sides of FIG. 5).

Referring to FIG. 5, a medical device $MD_X$ may authenticate and automatically pair with a control device. At block 502, a medical device $MD_X$ may not be associated with and/or in the line-of-sight of any control device. At block 504, the medical device $MD_X$ may periodically transmit its identifier $MD_X$ ID over its optical communication channel (e.g., IR channel) and wireless communication channel (e.g., RF channel). Periodically as described herein, may refer to a regularly occurring interval or time period (e.g., every "X" seconds, every "Y" minutes, and/or the like). According to further aspects, the medical device $MD_X$ may be configured to manually transmit its identifier $MD_X$ ID (e.g., upon a user actuating a transmit ID button on the medical device $MD_X$) over its optical communication channel (e.g., IR channel) and wireless communication channel (e.g., RF channel). At block 506, the medical device $MD_X$ may periodically sniff for incoming control device identifiers (e.g., CD IDs) over its optical communication channel. According to further aspects, the medical device $MD_X$ may be configured to manually sniff for incoming control device identifiers (e.g., CD IDs) over its optical communication channel (e.g., upon a user actuating a receive ID button on the medical device $MD_X$). At block 508, the medical device $MD_X$ and a control device $CD_X$ may be positioned in a line-of-sight of one another. At block 510, the medical device $MD_X$ may receive a control device identifier $CD_X$ ID over its optical communication channel. At block 512, the medical device $MD_X$ may scan its wireless communication channel for the control device identifier $CD_X$ ID. At decision block 514, the medical device $MD_X$ may determine whether it is receiving the same control device identifier $CD_X$ ID over its optical communication channel and its wireless communication channel. If it is determined, at decision block 514, that the received control device identifier $CD_X$ ID does not match any control device identifier being received over its wireless communication channel, the medical device $MD_X$ may continue to periodically sniff for incoming control device identifiers (e.g., CD IDs) over its optical communication channel at block 506. If it is determined, at decision block 514, that the optically received control device identifier $CD_X$ ID does match a control device identifier being received over its wireless communication channel, the medical device $MD_X$ may automatically associate with the control device $CD_X$ over its wireless communication channel at block 516. According to various aspects, the medical device $MD_X$ may store the association as pairing data (FIG. 2B, reference 276) in its data storage device (FIG. 2B, reference 262). At block 518 (e.g., shown in phantom as optional), the medical device $MD_X$ may display a visual indicator of its association with a control device. According to some aspects, the visual indicator may be a light emitting diode (LED) that illuminates when the medical device $MD_X$ is associated with a control device. According to another aspect, the visual indicator may flash when the medical device $MD_X$ is sniffing for a control device over its optical channel and illuminate without flashes when the medical device $MD_X$ is associated with a control device over its wireless channel. According to yet further aspects, the visual indicator may include a display that indicates the control device(s) to which it is associated. At block 520, after being authentically paired with the control device $CD_X$, the medical device $MD_X$ may transmit status information to the control device $CD_X$ and/or receive control inputs or commands from the control device $CD_X$.

Referring still to FIG. 5, a control device $CD_X$ may authenticate and automatically pair with a medical device. At block 532, a control device $CD_X$ may not be associated with and/or in the line-of-sight of any medical device. At block 534, the control device $CD_X$ may periodically transmit its identifier $CD_X$ ID over its optical communication channel (e.g., IR channel) and wireless communication channel (e.g., RF channel). Periodically as described herein, may refer to a regularly occurring interval or time period (e.g., every "X" seconds, every "Y" minutes, and/or the like). According to further aspects, the control device $CD_X$ may be configured to manually transmit its identifier $CD_X$ ID (e.g., upon a user actuating a transmit ID button on the control device $CD_X$) over its optical communication channel (e.g., IR channel) and wireless communication channel (e.g., RF channel). At block 536, the control device $CD_X$ may periodically sniff for incoming medical device identifiers (e.g., MD IDs) over its optical communication channel. According to further aspects, the control device $CD_X$ may be configured to manually sniff for incoming medical device identifiers (e.g., MD IDs) over its optical communication channel (e.g., upon a user actuating a receive ID button on the control device $CD_X$). At block 508, the control device $CD_X$ and a medical device $MD_X$ may be positioned in a line-of-sight of one another. At block 540, the control device $CD_X$ may receive a medical device identifier $MD_X$ ID over its optical communication channel. At block 542, the control device $CD_X$ may scan its wireless communication channel for the medical device identifier $MD_X$ ID. At decision block 544, the control device $CD_X$ may determine whether it is receiving the same medical device identifier $MD_X$ ID over its optical communication channel and its wireless communication channel. If it is determined, at decision block 544, that the optically received medical device identifier $MD_X$ ID does not match any medical device identifier being received over its wireless communication channel, the control device $CD_X$ may continue to periodically sniff for incoming medical device identifiers (e.g., MD IDs) over its optical communication channel at block 536. If it is determined, at decision block 544, that the received medical device identifier $MD_X$ ID does match a medical device identifier being received over its wireless communication channel, the control device $CD_X$ may automatically associate with the medical device $MD_X$ over its wireless communication channel at block 546. According to various aspects, the control device $CD_X$ may store the association as pairing data (FIG. 2A, reference 226) in its data storage device (FIG. 2A, reference 212). At block 548 (e.g., shown in phantom as optional), the control device $CD_X$ may display a visual indicator of its association with a medical device. According to some aspects, the visual indicator may be a light emitting diode (LED) that illuminates when the control device $CD_X$ is associated with a medical device. According to another aspect, the visual indicator may flash when the control device $CD_X$ is sniffing for a medical device over its optical channel and illuminate without flashes when the control device $CD_X$ is associated with a medical device over its wireless channel. According to yet further aspects, the visual indicator may include a display that indicates the medical device(s) to which it is associated. At block 550, after being authentically paired with the medical device $MD_X$, the control device $CD_X$ may transmit or issue control inputs or commands to the medical device $MD_X$ and/or receive status information from the medical device $MD_X$.

Still further, in view of FIG. 5, both the medical device $MD_X$ may authenticate and automatically pair with the control device $CD_X$ and the control device $CD_X$ may authenticate and automatically pair with the medical device $MD_X$, as described herein. According to various aspects of the present disclosure, the medical device $MD_X$ may not transmit status information to the control device $CD_X$ and/or receive control inputs or commands from the control device $CD_X$ and the control device CDX may not transmit or issue control inputs or commands to the medical device MDX and/or receive status information from the medical device MDX until such two-way authentication has occurred.

Figure 6:
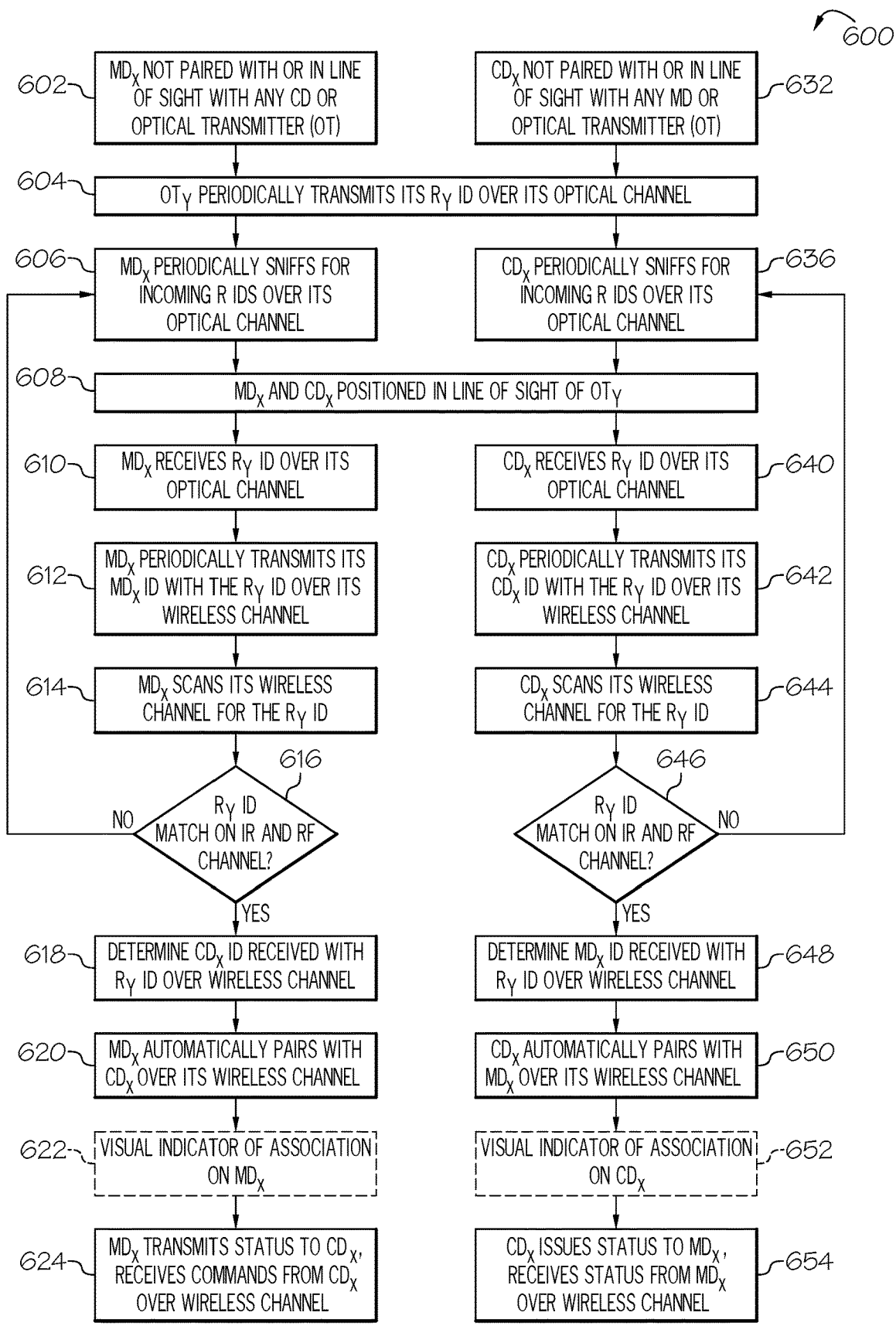
FIG. 6 depicts a flow diagram of another illustrative method for pairing a medical device and a control device using an optical communication channel, according to one or more embodiments shown and described herein.

FIG. 6 depicts a flow diagram of an illustrative method 600 for pairing a medical device and a control device using an optical communication channel, according to one or more embodiments of the present disclosure. In particular, FIG. 6 utilizes a separate optical transmitter OT (e.g., IR transmitter) to authentically pair the medical device and the control device. For example, an optical transmitter $OT_Y$ associated with room Y may broadcast a room identifier $R_Y$ ID as a beacon to the medical device(s) and the control device(s) within room Y such that only devices that receive the same beacon will attempt to pair with one another. According to various aspects, the optical transmitter OT may include a high power IR transmitter to ensure that the medical device(s) and the control device(s) receive the optical signal. According to further aspects, the optical transmitter OT may be physically located (e.g., ceiling of room, wall of room, and/or the like) to ensure that the medical device(s) and the control device(s) receive the optical signal. According to some aspects, a separate device within the room (e.g., the wall-mounted control unit 308, of FIG. 3) may function in a manner similar to the optical transmitter OT as described herein. Similar to FIG. 5, the pairing may include a one-way authentication of the medical device with a control device (e.g., left side of FIG. 6), a one-way authentication of the control device with a medical device (e.g., right side of FIG. 6), or a two-way authentication of the medical device and the control device (e.g., both sides of FIG. 6).

Referring to FIG. 6, a medical device $MD_X$ may authenticate and automatically pair with a control device using a separate optical transmitter. At block 602, a medical device $MD_X$ may not be associated with and/or in the line-of-sight of any control device CD and/or any optical transmitter OT (e.g., an IR transmitter). At block 604, an optical transmitter $OT_Y$ may periodically transmit its room identifier $R_Y$ ID over its optical communication channel (e.g., IR channel). Periodically as described herein, may refer to a regularly occurring interval or time period (e.g., every "X" seconds, every "Y" minutes, and/or the like). According to further aspects, the optical transmitter $OT_Y$ may be configured to manually transmit its room identifier $R_Y$ ID (e.g., upon a user actuating a transmit ID button on the optical transmitter $OT_Y$) over its optical communication channel (e.g., IR channel). At block 606, the medical device $MD_X$ may periodically sniff for incoming room identifiers (e.g., R IDs) over its optical communication channel (e.g. IR channel). According to further aspects, the medical device $MD_X$ may be configured to manually sniff for incoming room identifiers (e.g., R IDs) over its optical communication channel (e.g., upon a user actuating a receive ID button on the medical device $MD_X$). At block 608, the medical device $MD_X$ and a control device $CD_X$ may be positioned in the line-of-sight of the optical transmitter $OT_Y$. At block 610, the medical device $MD_X$ may receive the room identifier $R_Y$ ID over its optical communication channel. At block 612, the medical device $MD_X$ may periodically transmit its identifier $MD_X$ ID with the optically received room identifier $R_Y$ ID over its wireless communication channel (e.g., RF channel). According to further aspects, the medical device $MD_X$ may be configured to manually transmit its identifier $MD_X$ ID with the optically received room identifier $R_Y$ ID (e.g., upon a user actuating a transmit ID button on the medical device $MD_X$) over its wireless communication channel (e.g., RF channel). At block 614, the medical device $MD_X$ may scan its wireless communication channel for the optically received room identifier $R_Y$ ID. At decision block 616, the medical device $MD_X$ may determine whether it is receiving a same room identifier $R_Y$ ID over its optical communication channel and its wireless communication channel. If it is determined, at decision block 616, that the optically received room identifier $R_Y$ ID does not match any room identifier being received over its wireless communication channel, the medical device $MD_X$ may continue to periodically sniff for incoming room identifiers (e.g., R IDs) over its optical communication channel at block 606. If it is determined, at decision block 616, that the optically received room identifier $R_Y$ ID does match a room identifier being received over its wireless communication channel, the medical device $MD_X$ may determine a control device identifier $CD_X$ ID received with the matching $R_Y$ ID over its wireless communication network at block 618. At block 620, the medical device $MD_X$ may automatically pair with the control device $CD_X$ over its wireless communication channel. According to various aspects, the medical device $MD_X$ may store the association as pairing data (FIG. 2B, reference 276) in its data storage device (FIG. 2B, reference 262). At block 622 (e.g., shown in phantom as optional), the medical device $MD_X$ may display a visual indicator of its association with a control device. According to some aspects, the visual indicator may be a light emitting diode (LED) that illuminates when the medical device $MD_X$ is associated with a control device. According to another aspect, the visual indicator may flash when the medical device $MD_X$ is sniffing for a room identifier over its optical channel and illuminate without flashes when the medical device $MD_X$ is associated with a control device over its wireless channel. According to yet further aspects, the visual indicator may include a display that indicates the control device(s) to which it is associated. At block 624, after being authentically paired with the control device $CD_X$, the medical device $MD_X$ may transmit status information to the control device $CD_X$ and/or receive control inputs or commands from the control device $CD_X$.

Referring still to FIG. 6, a control device $CD_X$ may authenticate and automatically pair with a medical device using a separate optical transmitter. At block 632, a control device $CD_X$ may not be associated with and/or in the line-of-sight of any medical device MD and/or any optical transmitter OT (e.g., an IR transmitter). At block 604, an optical transmitter $OT_Y$ may periodically transmit its room identifier $R_Y$ ID over its optical communication channel (e.g., IR channel). Periodically as described herein, may refer to a regularly occurring interval or time period (e.g., every "X" seconds, every "Y" minutes, and/or the like). According to further aspects, the optical transmitter $OT_Y$ may be configured to manually transmit its room identifier $R_Y$ ID (e.g., upon a user actuating a transmit ID button on the optical transmitter $OT_Y$) over its optical communication channel (e.g., IR channel). At block 636, the control device $CD_X$ may periodically sniff for incoming room identifiers (e.g., R IDs) over its optical communication channel (e.g. IR channel). According to further aspects, the control device $CD_X$ may be configured to manually sniff for incoming room identifiers (e.g., R IDs) over its optical communication channel (e.g., upon a user actuating a receive ID button on the control device $CD_X$). At block 608, the control device $CD_X$ and a medical device $MD_X$ may be positioned in the line-of-sight of the optical transmitter $OT_Y$. At block 640, the control device $CD_X$ may receive the room identifier $R_Y$ ID over its optical communication channel. At block 642, the control device $CD_X$ may periodically transmit its identifier $CD_X$ ID with the optically received room identifier $R_Y$ ID over its wireless communication channel (e.g., RF channel). According to further aspects, the control device $CD_X$ may be configured to manually transmit its identifier $CD_X$ ID with the optically received room identifier $R_Y$ ID (e.g., upon a user actuating a transmit ID button on the control device $CD_X$) over its wireless communication channel (e.g., RF channel). At block 644, the control device $CD_X$ may scan its wireless communication channel for the optically received room identifier $R_Y$ ID. At decision block 646, the control device $CD_X$ may determine whether it is receiving a same room identifier $R_Y$ ID over its optical communication channel and its wireless communication channel. If it is determined, at decision block 646, that the optically received room identifier $R_Y$ ID does not match any room identifier being received over its wireless communication channel, the control device $CD_X$ may continue to periodically sniff for incoming room identifiers (e.g., R IDs) over its optical communication channel at block 636. If it is determined, at decision block 646, that the optically received room identifier $R_Y$ ID does match a room identifier being received over its wireless communication channel, the control device $CD_X$ may determine a medical device identifier $MD_X$ ID received with the matching $R_Y$ ID over its wireless communication network at block 648. At block 650, the control device $CD_X$ may automatically pair with the medical device $MD_X$ over its wireless communication channel. According to various aspects, the control device $CD_X$ may store the association as pairing data (FIG. 2A, reference 226) in its data storage device (FIG. 2A, reference 212). At block 652 (e.g., shown in phantom as optional), the control device $CD_X$ may display a visual indicator of its association with a medical device. According to some aspects, the visual indicator may be a light emitting diode (LED) that illuminates when the control device $CD_X$ is associated with a medical device. According to another aspect, the visual indicator may flash when the control device $CD_X$ is sniffing for a room identifier over its optical channel and illuminate without flashes when the control device $CD_X$ is associated with a medical device over its wireless channel. According to yet further aspects, the visual indicator may include a display that indicates the medical device(s) to which it is associated. At block 654, after being authentically paired with the medical device $MD_X$, the control device $CD_X$ may transmit or issue control inputs or commands to the medical device $MD_X$ and/or receive status information from the medical device $MD_X$.

Still further, in view of FIG. 6, both the medical device $MD_X$ may authenticate and automatically pair with the control device $CD_X$ and the control device $CD_X$ may authenticate and automatically pair with the medical device $MD_X$, as described herein. According to various aspects of the present disclosure, the medical device $MD_X$ may not transmit status information to the control device $CD_X$ and/or receive control inputs or commands from the control device $CD_X$ and the control device $CD_X$ may not transmit or issue control inputs or commands to the medical device $MD_X$ and/or receive status information from the medical device $MD_X$ until such two-way authentication has occurred.

Yet further in view of FIG. 6, according to an alternative aspect, the optical transmitter OT may be substituted with an Ultra-Wide Band (UWB) transmitter. Similar to above, the UWB transmitter may broadcast a room identifier RX ID as a location beacon to the devices (e.g., medical device(s) and the control device(s)) within room X and the devices may use an UWB communication channel to receive the location beacon, such that only devices that receive the same beacon will attempt to pair with one another.

Figure 7:
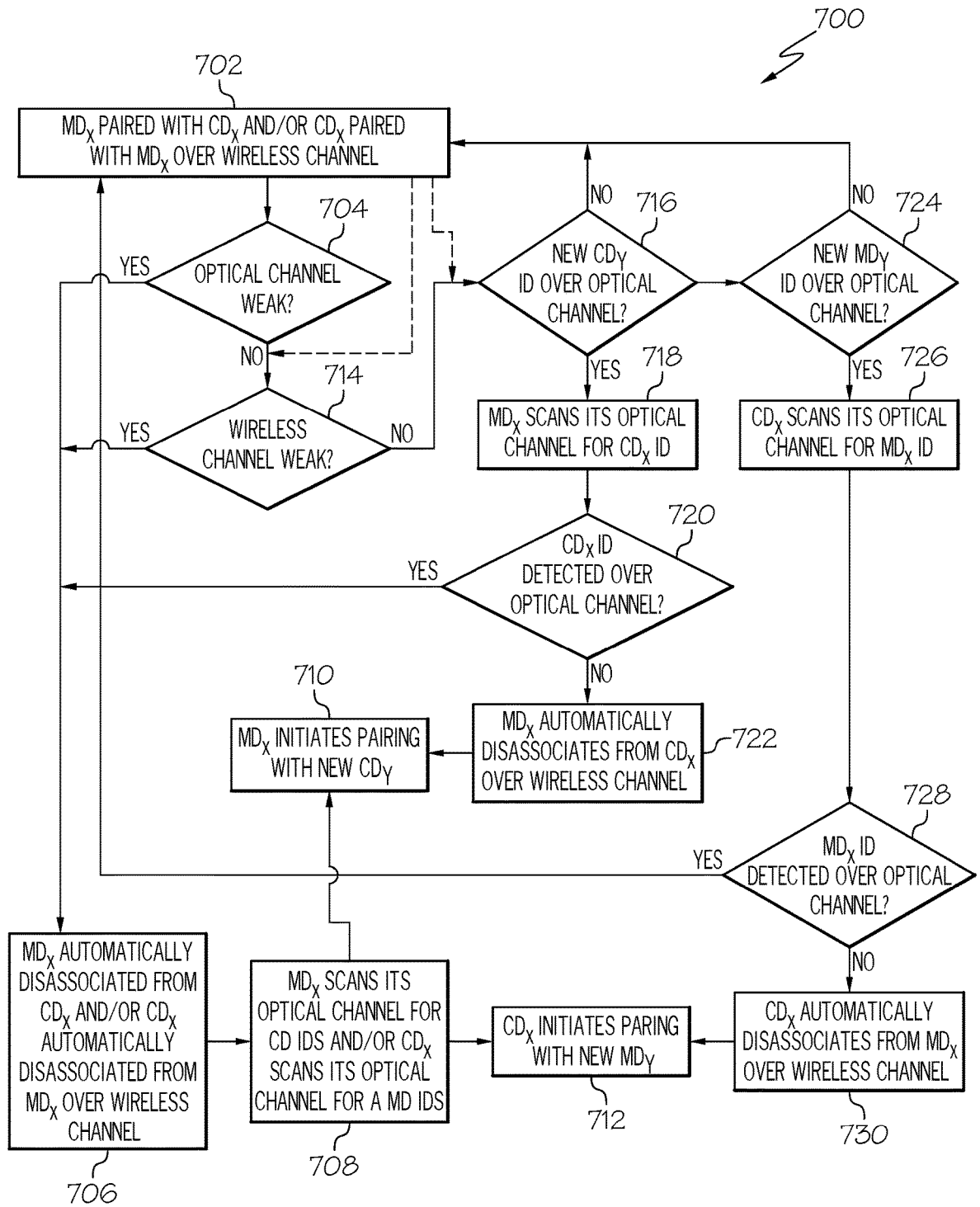
FIG. 7 depicts a flow diagram of an illustrative method for associating and disassociating medical devices and control devices, according to one or more embodiments shown and described herein.

FIG. 7 depicts a flow diagram of an illustrative method 700 for associating and disassociating medical devices and control devices, according to one or more embodiments of the present disclosure. Referring to FIG. 7, at block 702, a medical device $MD_X$ may be authentically paired with a control device $CD_X$ over a wireless communication channel (e.g., RF channel) and/or the control device $CD_X$ may be authentically paired with the medical device $MD_X$ over the wireless communication channel, as described herein. At decision block 704, the medical device $MD_X$ may determine whether an optical communication channel (e.g., IR channel) with the authentically paired control device $CD_X$ is weak (e.g., below a predetermined threshold optical signal strength) or the control device $CD_X$ may determine whether the optical communication channel with the authentically paired medical device $MD_X$ is weak (e.g., below a predetermined threshold optical signal strength). In such aspects, the medical device $MD_X$ and/or the $CD_X$ may be configured to use the optical communication channel as a cue that the medical device $MD_X$ and/or the $CD_X$ is being repositioned within the medical facility (e.g., rail-mounted lift 302 of FIG. 3 translated into adjoining room, wireless hand control unit 306 of FIG. 3 carried outside of room by a caregiver, and/or the like). If it is determined at decision block 704 that the optical communication channel is weak, the medical device $MD_X$ may be configured to automatically disassociate from the control device $CD_X$ over the wireless communication channel and/or the control device $CD_X$ may be configured to automatically disassociate from the medical device $MD_X$ over the wireless communication channel at block 706. According to further aspects, the medical device $MD_X$ may be configured to manually disassociate (e.g., upon a user actuating a disassociate button on the medical device $MD_X$) from a control device $CD_X$ and/or the control device $CD_X$ may be configured to manually disassociate (e.g., upon a user actuating a disassociate button on the control device $CD_X$) from a medical device $MD_X$. Upon disassociation, at block 708, the medical device $MD_X$ may scan its optical communication channel for control device identifiers (e.g., CD IDs) and, at block 710, the medical device MDX may initiate an authenticated pairing with a new control device (e.g., $CD_Y$), as described herein. Similarly upon disassociation, at block 708, the control device $CD_X$ may scan its optical communication channel for medical device identifiers (e.g., MD IDs) and, at block 712, the control device $CD_X$ may initiate an authenticated pairing with a new medical device (e.g., $MD_Y$), as described herein. If it is determined at decision block 704 that the optical communication channel is not weak, the medical device $MD_X$ may determine whether a wireless communication channel (e.g., RF channel) with the authentically paired control device $CD_X$ is weak (e.g., below a predetermined threshold wireless signal strength) and/or the control device $CD_X$ may determine whether the wireless communication channel with the authentically paired medical device MDX is weak (e.g., below a predetermined threshold wireless signal strength) at decision block 714. If it is determined at decision block 714 that the wireless communication channel is weak, the medical device $MD_X$ may be similarly configured to automatically disassociate from the control device $CD_X$ over the wireless communication channel and/or the control device $CD_X$ may be similarly configured to automatically disassociate from the medical device $MD_X$ over the wireless communication channel at block 706. At block 708, the medical device $MD_X$ may scan its optical communication channel for control device identifiers (e.g., CD IDs) and, at block 710, the medical device $MD_X$ may initiate an authenticated pairing with a new or different control device (e.g., $CD_Y$) as described. Likewise, at block 708, the control device $CD_X$ may scan its optical communication channel for medical device identifiers (e.g., MD IDs) and, at block 712, the control device $CD_X$ may initiate an authenticated pairing with a new or different medical device (e.g., $MD_Y$) as described. According to an alternative aspect (e.g., shown in phantom) the method may proceed from block 702 directly to decision block 714 and proceed as described herein. In such an aspect, the medical device $MD_X$ may remain authentically paired with the control device $CD_X$ over the wireless communication channel irrespective of whether the optical communication channel with the authentically paired control device $CD_X$ is weak or broken and/or the control device $CD_X$ may remain authentically paired with the medical device $MD_X$ over the wireless communication channel irrespective of whether the optical communication channel with the authentically paired medical device $MD_X$ is weak or broken. For example, the medical device $MD_X$ or the control device $CD_X$ may maintain communications (e.g., non-control based communications such as battery status or the like) over the wireless communication channel with the control device $CD_X$ or the medical device $MD_X$, respectively, despite the optical communication channel being weak or broken (e.g., due to the control device $CD_X$ or the medical device $MD_X$, respectively, being in a cabinet or the optical communication path being blocked or interfered with in some way). At decision block 714, if it is determined that the wireless communication channel is not weak the medical device $MD_X$ may determine whether a new or different $CD_Y$ ID is being received over its optical communication channel at decision block 716. According to an alternative aspect (e.g. shown in phantom) the method may proceed from block 702 directly to decision block 716. If it is determined at decision block 716 that no new or different $CD_Y$ ID is being received over its optical communication channel, the medical device $MD_X$ may remain authentically paired with the control device $CD_X$ over its wireless communication channel at block 702. If it is determined at decision block 716 that a new or different $CD_Y$ ID is being received over its optical communication channel, the medical device $MD_X$ may be configured to scan its optical channel for the $CD_X$ ID associated with its authentically paired control device $CD_X$ at block 718. At decision block 720, if it is determined that the $CD_X$ ID has been detected, the medical device $MD_X$ may remain authentically paired with the control device $CD_X$ over its wireless communication channel at block 702. According to the aspects described in FIG. 7, the medical device $MD_X$ may only be authentically paired with one control device. Such an embodiment may prevent the medical device MDX from receiving control inputs (e.g., simultaneous control inputs, conflicting control inputs, and/or the like) from more than one control device. Here, it should be appreciated that other embodiments may include the medical device $MD_X$ as authentically paired with multiple control devices (e.g., dual lift capability, two control devices operating in tandem). At decision block 720, if it is determined that the $CD_X$ ID has not been detected, the medical device $MD_X$ may automatically disassociate from the control device $CD_X$ over its wireless communication channel at block 722, and at block 710, the medical device $MD_X$ may initiate an authenticated pairing with the new or different control device $CD_Y$, as described. Similarly, at decision block 724, the control device $CD_X$ may determine whether a new or different $MD_Y$ ID is being received over its optical communication channel. In such aspects, as depicted in FIG. 7, decision block 716 may be a pass-through to decision block 724 (e.g., the control device $CD_X$ may not monitor its optical communication channel for any new or different control device $CD_Y$). As such, similar to as described herein, the control device $CD_X$, may determine whether a new or different $MD_Y$ ID is being received over its optical communication channel directly from block 702 and/or if it is determined at decision block 714 that the wireless communication channel is not weak. If it is determined at decision block 724 that no new or different $MD_Y$ ID is being received over its optical communication channel, the control device $CD_X$ may remain authentically paired with the medical device $MD_X$ over its wireless communication channel at block 702. If it is determined at decision block 724 that a new or different $MD_Y$ ID is being received over its optical communication channel, the control device $CD_X$ may be configured to scan its optical channel for the $MD_X$ ID associated with its authentically paired medical device $MD_X$ at block 726. At decision block 728, if it is determined that the $MD_X$ ID has been detected, the control device $CD_X$ may remain authentically paired with the medical device $MD_X$ over its wireless communication channel at block 702. According to the aspects described in FIG. 7, the control device $CD_X$ may only be authentically paired with one medical device. Such an embodiment may prevent the control device $CD_X$ from transmitting control inputs to more than one medical device. Here, it should be appreciated that other embodiments may include the control device $CD_X$ as authentically paired with multiple medical devices (e.g. in the same room). At decision block 728, if it is determined that the $MD_X$ ID has not been detected, the control device $CD_X$ may automatically disassociate from the medical device $MD_X$ over its wireless communication channel at block 730, and at block 712, the control device $CD_X$ may initiate an authenticated pairing with the new or different medical device $MD_Y$, as described.

Figure 8:
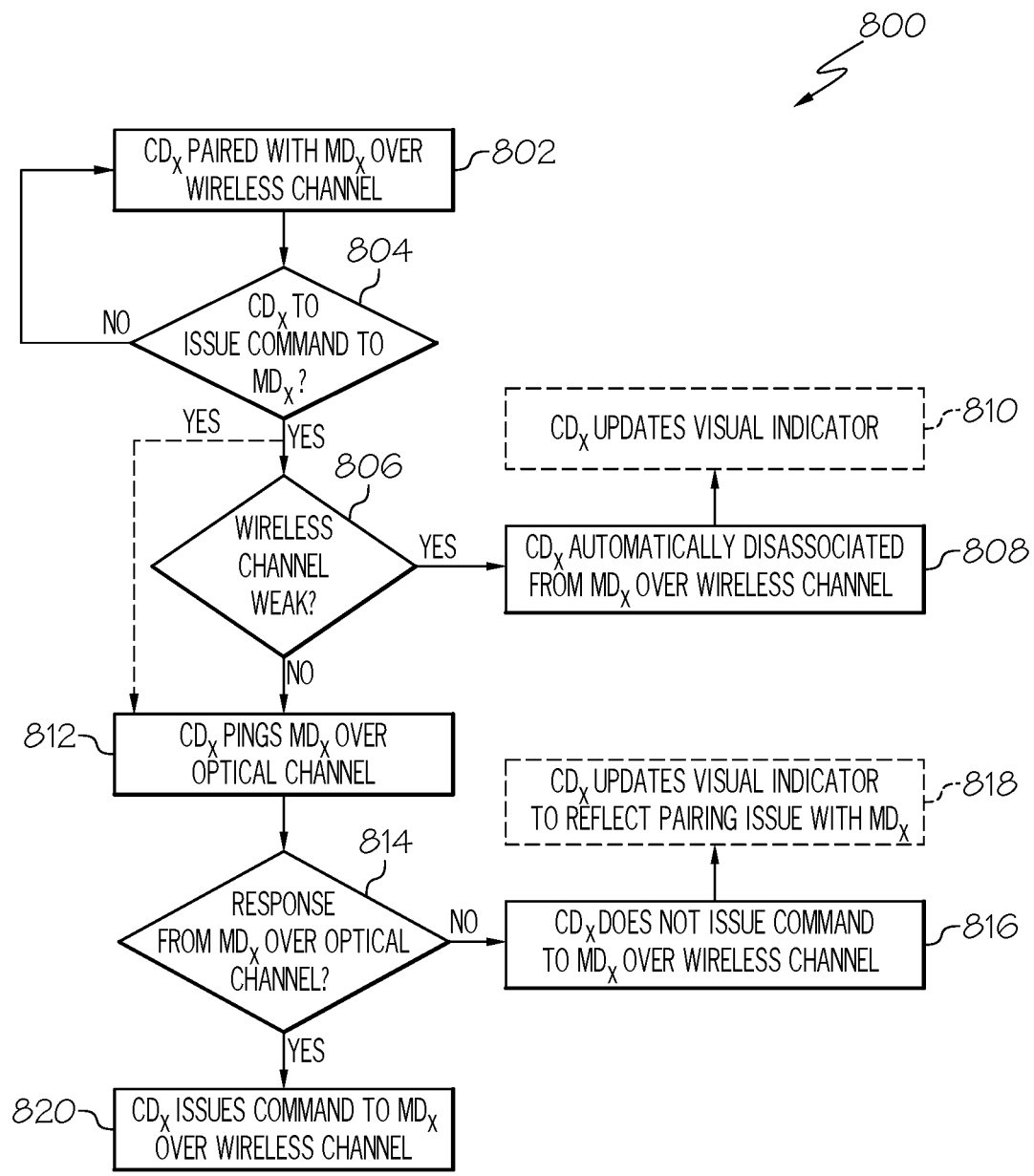
FIG. 8 depicts a flow diagram of an illustrative method for a control device to issue commands or control inputs to an authentically paired medical device, according to one or more embodiments shown and described herein.

FIG. 8 depicts a flow diagram of an illustrative method 800 for a control device to issue commands or control inputs to an authentically paired medical device, according to one or more embodiments of the present disclosure. According to various aspects, method 800 may be utilized for all control functions or only subject critical functions (e.g., actuating a motor, turning on a pump, and/or the like). Referring to FIG. 8, at block 802, a control device $CD_X$ may be authentically paired with a medical device $MD_X$ over its wireless communication channel, as described herein. At decision block 804, the control device $CD_X$ may be configured to determine (e.g., based on inputs received via user interface controls 246 of FIG. 2A) whether a command or control input is to be issued or transmitted to the medical device $MD_X$. If it is determined that a command or control input is not to be issued or transmitted to the medical device $MD_X$, the control device $CD_X$ may remain paired with the $MD_X$ over its wireless communication channel at block 802. If it is determined that a command or control input is to be issued or transmitted to the medical device $MD_X$, the control device $CD_X$ may be configured to determine whether the wireless communication channel is weak (e.g., below a predetermined threshold wireless signal strength) at decision block 806. If it is determined that the wireless communication channel is weak, the control device $CD_X$ may be configured to automatically disassociate from the medical device MDX over the wireless communication channel at block 808. At block 810 (shown in phantom as an optional step), the control device $CD_X$ may be configured to update its visual indicator to reflect the disassociation (e.g., LED off). If it is determined that the wireless communication channel is not weak, the control device $CD_X$ may be configured, at block 812, to ping the medical device $MD_X$ over its optical communication channel (e.g., transmit an inquiry token). According to an alternative aspect (e.g., shown in phantom) the method may proceed from decision block 804 directly to block 812 and proceed as described herein. At decision block 814, the control device $CD_X$ may be configured to determine whether it has received a response (e.g., response token, MD ID, and/or the like) from the medical device $MD_X$ over its optical communication channel. If it is determined that the control device $CD_X$ has not received a response from the medical device $MD_X$, the control device $CD_X$ may be configured, at block 816, to not issue or transmit the command or control input to the medical device $MD_X$. At block 818 (shown in phantom as an optional step), the control device $CD_X$ may be configured to update its visual indicator to reflect a pairing issue with the medical device $MD_X$ (e.g., medical device $MD_X$ not within line-of-sight of control device $CD_X$, indicator that the medical device $MD_X$ must be re-located to within the line-of-sight of the control device $CD_X$ to execute a control function). If it is determined that the control device $CD_X$ has received a response from the medical device $MD_X$, the control device $CD_X$ may be configured to, at block 820, issue the command or control input to the medical device $MD_X$ over its wireless communication channel. According to such aspects, if a medical device $MD_X$ is moved into an adjacent room (e.g., no longer within line-of-sight of the control device $CD_X$) the control device $CD_X$ is rendered unable to issue a command or control input to the medical device (MDX) despite being otherwise able to over a strong wireless communication channel.

According to another embodiment, referring back to FIGS. 2A and 2B, the control device 200 may include a location system 234 and the medical device 250 may include a location system 284. In such aspects, the medical device 250 and/or the control device 200 may be configured to further transmit their respective location information (e.g., MD LOC, CD LOC) with their respective identifiers (e.g., MD ID, CD ID) as described herein. In such aspects, the medical device 250 may be configured to compare a received CD LOC with its MD LOC as part of its determination as to whether to authentically pair with a control device. In some aspects, an initial range (e.g., about 2 m to about 5 m radius) may be used for initial authentication and a control range (e.g., average size of room) may be used for disassociation. In further aspects, the medical device 250 may be configured to adjust/correct its MD LOC as well as the received CD LOC using a medical facility location MF LOC location beacon with known coordinates. Similarly, the control device 200 may be configured to compare a received MD LOC with its CD LOC as part of its determination as to whether to authentically pair with a medical device. Again, an initial range (e.g., about 2 m to about 5 m radius) may be used for initial authentication and a control range (e.g., average size of room) may be used for disassociation. Likewise, the control device 200 may be configured to adjust/correct its CD LOC as well as the received MD LOC using a medical facility location MF LOC location beacon with known coordinates. According to various embodiments, such aspects may be used to further confirm the other authentication methods as described herein.

According to the various embodiments described herein, each of the optical communication channel (e.g., IR channel) and the wireless communication channel (e.g., RF channel) may be configured as a single-path communication channel or a dual-path communication channel. Furthermore, although the line-of-sight communication channel is described herein as an optical communication channel, the line-of sight communication channel may be any auxiliary line-of-sight communication channel that is guaranteed to be line-of-sight only. Namely, the line-of-sight communication channel is only accessible to the device to be controlled (e.g., medical device) when visible from a control point (e.g., control device).

It should now be understood that the systems and methods described herein are suitable for pairing a medical device and a control device using a line-of-sight optical link (e.g., IR channel). In particular, the systems and methods described herein automatically authenticate a configurable, pairable wireless connection (e.g. RF channel) to be used to execute control actions for a medical device (e.g., rail-mounted lift) to ensure that the control inputs are coming from a control device (e.g., a tethered hand control unit, a wireless hand control unit, a wall-mounted control unit, a sling bar control unit, a coupling control unit, and/or the like) located in the same room as the medical device. Such systems and methods ensure that the control inputs coming from the control device are only directed to a medical device that is directly observable or visible to the control device user.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for automatically pairing a medical device with control devices, the method comprising:
receiving, via a first communication channel, a first identifier associated with a first control device within a line-of-sight of the medical device;
receiving, via a second communication channel different from the first communication channel, at least one identifier associated with at least one control device;
determining that the identifier received over the first communication channel matches an identifier of the at least one identifier received over the second communication channel;
automatically pairing with the first control device associated with the matching identifier over the second communication channel
receiving, via the first communication channel, a second identifier associated with a second control device within the line-of-sight of the medical device;
determining whether the first identifier is detectable over the first communication channel; and
remaining paired with the first control device if the first identifier is detected over the first communication channel; or
automatically disassociating from the first control device if the first identifier is not detected over the first communication channel.

2. The method of claim 1, wherein the first communication channel is an optical communication channel and the second communication channel is a wireless communication channel.

3. The method of claim 2, wherein the optical communication channel is an infrared (IR) communication channel and the wireless communication channel is a radio frequency (RF) communication channel.

4. The method of claim 1, further comprising:
receiving control inputs from the first control device associated with the matching identifier, the control inputs for controlling a function of the medical device.

5. The method of claim 1, further comprising:
determining that at least one of the first communication channel or the second communication channel is associated with a signal below a predetermined threshold strength; and
disassociating from the first control device associated with the matching identifier.

6. The method of claim 1, further comprising:
determining that the second identifier received over the first communication channel matches an identifier of the at least one identifier received over the second communication channel; and
automatically pairing with the second control device associated with the matching second identifier over the second communication channel.

7. A method for automatically pairing a control device with medical devices, the method comprising:
receiving, via a first communication channel, a first identifier associated with a first medical device within a line-of-sight of the control device;
receiving, via a second communication channel different from the first communication channel, at least one identifier associated with at least one medical device;
determining that the first identifier received over the first communication channel matches an identifier of the at least one identifier received over the second communication channel;
automatically pairing with the first medical device associated with the matching identifier over the second communication channel
receiving, via the first communication channel, a second identifier associated with a second medical device within the line-of-sight of the control device;
determining whether the first identifier is detectable over the first communication channel; and
remaining paired with the first medical device if the first identifier is detected over the first communication channel; or
automatically disassociating from the first medical device if the first identifier is not detected over the first communication channel.

8. The method of claim 7, wherein the first communication channel is an optical communication channel and the second communication channel is a wireless communication channel.

9. The method of claim 8, wherein the optical communication channel is an infrared (IR) communication channel and the wireless communication channel is a radio frequency (RF) communication channel.

10. The method of claim 7, further comprising:
transmitting control inputs to the first medical device associated with the matching identifier, the control inputs for controlling a function of the first medical device.

11. The method of claim 7, further comprising:
determining that at least one of the first communication channel or the second communication channel is associated with a signal below a predetermined threshold strength; and
disassociating from the first medical device associated with the matching identifier.

12. The method of claim 7, further comprising:
determining that the second identifier received over the first communication channel matches an identifier of the at least one identifier received over the second communication channel; and
automatically pairing with the second medical device associated with the matching second identifier over the second communication channel.

13. The method of claim 7, further comprising:
receiving, via at least one user interface control, a control input;
sending, via the first communication channel, an inquiry token to the first medical device associated with the matching identifier;
determining, via the first communication channel, whether a response token has been received from the first medical device associated with the matching identifier; and
transmitting the control input to the first medical device associated with the matching identifier if the response token has been received over the first communication channel; or abstaining from transmitting the control input to the first medical device associated with the matching identifier if the response token has not been received over the first communication channel.

14. The method of claim 7, further comprising:
updating a visual indicator to reflect that the first medical device is not within a line-of-sight of the control device.

15. A method for automatically pairing devices, the method comprising:
transmitting, via a transmitter positioned within a location, a location identifier over a first communication channel to devices with a line-of-sight of the transmitter;
receiving, by a first device and a second device, the location identifier over the first communication channel;
transmitting, by the first device, the location identifier and an identifier associated with the first device over a second communication channel;
transmitting, by the second device, the location identifier and an identifier associated with the second device over the second communication channel;
scanning, by the first device and the second device, the second communication channel for the location identifier received over the first communication channel;
determining, by the first device and the second device, that the location identifier received over the first communication channel matches a location identifier on the second communication channel;
determining, by the first device, the second device identifier associated with the matching location identifier and automatically pairing with the second device associated with the second device identifier over the second communication channel; and
determining, by the second device, the first device identifier associated with the matching location identifier, and automatically pairing with the first device associated with the first device identifier over the second communication channel.

16. The method of claim 15, wherein the first communication channel is an optical communication channel and the second communication channel is a wireless communication channel.

17. The method of claim 16, wherein the optical communication channel is an infrared (IR) communication channel and the wireless communication channel is a radio frequency (RF) communication channel.

18. The method of claim 15, wherein the first communication channel is an ultra-wide band communication channel.

* * * * *